US010621280B2

(12) United States Patent
Jain et al.

(10) Patent No.: US 10,621,280 B2
(45) Date of Patent: Apr. 14, 2020

(54) CUSTOMIZED DYNAMIC USER FORMS

(71) Applicant: Vignet Incorporated, Fairfax, VA (US)

(72) Inventors: Neeta Jain, Fairfax, VA (US); Yue Cao, Vienna, VA (US); Dave Klein, Oakton, VA (US); Praduman Jain, Fairfax, VA (US)

(73) Assignee: Vignet Incorporated, Fairfax, VA (US)

( * ) Notice: Subject to any disclaimer, the term of this patent is extended or adjusted under 35 U.S.C. 154(b) by 0 days.

(21) Appl. No.: 15/935,276

(22) Filed: Mar. 26, 2018

(65) Prior Publication Data

US 2018/0210870 A1 Jul. 26, 2018

Related U.S. Application Data

(62) Division of application No. 15/279,845, filed on Sep. 29, 2016, now Pat. No. 9,928,230.

(51) Int. Cl.
*G06F 17/24* (2006.01)
*G06F 17/22* (2006.01)
*G06F 17/21* (2006.01)
*G06F 17/27* (2006.01)
*G16H 10/20* (2018.01)
*H04L 29/08* (2006.01)

(52) U.S. Cl.
CPC .......... *G06F 17/243* (2013.01); *G06F 17/211* (2013.01); *G06F 17/2229* (2013.01); *G06F 17/2288* (2013.01); *G06F 17/248* (2013.01); *G06F 17/2725* (2013.01); *G16H 10/20* (2018.01); *H04L 67/06* (2013.01); *H04L 67/10* (2013.01)

(58) Field of Classification Search
CPC .................................................. G06F 17/243
See application file for complete search history.

(56) References Cited

U.S. PATENT DOCUMENTS

| 6,029,195 | A | 2/2000 | Herz |
| 7,330,717 | B2 | 2/2008 | Gidron et al. |
| 7,827,478 | B2 | 11/2010 | Farr et al. |
| 7,827,495 | B2 | 11/2010 | Bells et al. |

(Continued)

OTHER PUBLICATIONS

Final Office Action in U.S. Appl. No. 15/040,635, dated Apr. 13, 2017, 13 pages.

(Continued)

*Primary Examiner* — Asher D Kells
(74) *Attorney, Agent, or Firm* — Fish & Richardson P.C.

(57) ABSTRACT

In some implementations, a system dynamically adjusts an electronic form of an application based on user data and form data specified for the electronic form. Form data that specifies characteristics of the electronic form is initially received by a computing device. The form data specifies one or more rules configured to vary the content of the electronic form that is presented for different users. User data indicating characteristics of a user is then obtained by the computing device. An interactive element is then selected from among a set of multiple interactive elements based on the received user data and the rules in the received form data. A view of the electronic form is customized for the user by including, in the customized view, the interactive element. The view of the customized electronic form is then displayed by the computing device.

25 Claims, 9 Drawing Sheets

(56) References Cited

U.S. PATENT DOCUMENTS

| | | | |
|---|---|---|---|
| 8,078,956 B1* | 12/2011 | Feldman | G06F 17/2247 715/223 |
| 8,850,304 B2 | 9/2014 | Ye et al. | |
| 9,256,698 B2 | 2/2016 | Vincent, III | |
| 9,361,011 B1 | 6/2016 | Burns | |
| 9,426,433 B1 | 8/2016 | Mazzarella | |
| 9,461,972 B1 | 10/2016 | Mehta | |
| 9,928,230 B1 | 3/2018 | Jain et al. | |
| 2001/0019338 A1 | 9/2001 | Roth | |
| 2002/0022973 A1 | 2/2002 | Sun | |
| 2004/0073868 A1 | 4/2004 | Easter et al. | |
| 2005/0086587 A1 | 4/2005 | Balz | |
| 2005/0186550 A1 | 8/2005 | Gillani | |
| 2006/0107219 A1 | 5/2006 | Ahya | |
| 2008/0005679 A1 | 1/2008 | Rimas-Ribikauskas | |
| 2008/0127040 A1 | 5/2008 | Barcellona | |
| 2009/0024944 A1 | 1/2009 | Louch | |
| 2009/0043689 A1 | 2/2009 | Yang | |
| 2009/0094052 A1 | 4/2009 | James et al. | |
| 2009/0163182 A1 | 6/2009 | Gatti | |
| 2009/0172002 A1 | 7/2009 | Bathiche | |
| 2010/0041378 A1 | 2/2010 | Aceves | |
| 2011/0200979 A1 | 8/2011 | Benson | |
| 2012/0102050 A1 | 4/2012 | Button | |
| 2012/0272156 A1 | 10/2012 | Kerger | |
| 2013/0110565 A1 | 5/2013 | Means | |
| 2013/0166494 A1 | 6/2013 | Davis | |
| 2013/0238686 A1 | 9/2013 | O'Donoghue | |
| 2014/0088995 A1 | 3/2014 | Damani | |
| 2014/0100883 A1 | 4/2014 | Hamilton | |
| 2014/0156823 A1 | 6/2014 | Liu | |
| 2014/0181715 A1 | 6/2014 | Axelrod | |
| 2014/0240122 A1 | 8/2014 | Roberts | |
| 2014/0273913 A1 | 9/2014 | Michel | |
| 2015/0135160 A1 | 5/2015 | Gauvin | |
| 2015/0220233 A1 | 8/2015 | Kok et al. | |
| 2016/0058287 A1 | 3/2016 | Dyell | |
| 2017/0286389 A1* | 10/2017 | Ceneviva | G06F 17/248 |
| 2018/0089159 A1 | 3/2018 | Jain et al. | |

OTHER PUBLICATIONS

Final Office Action in U.S. Appl. No. 15/152,411, dated Mar. 17, 2017, 17 pages.

http://www.khanacademic.org, 2017, 1 page.

Non-Final Office Action in U.S. Appl. No. 15/040,635, dated Dec. 30, 2016, 11 pages.

Non-Final Office Action in U.S. Appl. No. 15/040,635, dated Jul. 8, 2016, 9 pages.

Non-Final Office Action in U.S. Appl. No. 15/067,046, dated Nov. 1, 2016, 19 pages.

Non-Final Office Action in U.S. Appl. No. 15/152,411, dated Dec. 7, 2016, 10 pages.

Non-Final Office Action in U.S. Appl. No. 15/279,845, dated Apr. 21, 2017, 10 pages.

Non-Final Office Action U.S. Appl. No. 15/337,222, dated Mar. 23, 2017, 13 pages.

Non-Final Office Action in U.S. Appl. No. 15/382,126, dated Mar. 17, 2017, 16 pages.

* cited by examiner

610

**FORM A – PERFORMANCE ANALYSIS
FOR ELECTRONIC FORM**

OVERALL COMPLETION RATE: 82%

612
> 50 YEARS OLD     62%
< 50 YEARS OLD     96%

AVERAGE TIME SPENT: 7 MIN

614
> 50 YEARS OLD     11 MIN
< 50 YEARS OLD     3 MIN

SUGGESTED FORM UPDATES

616
> 50 YEARS OLD     REDUCE FORM COMPLEXITY
< 50 YEARS OLD     MAINTAIN CURRENT FORM

FIG. 6

CUSTOMIZED DYNAMIC USER FORMS

CROSS-REFERENCE TO RELATED APPLICATIONS

This application is a divisional of U.S. application Ser. No. 15/279,845, filed Sep. 29, 2016, now allowed, the entire contents of which is hereby incorporated by reference in its entireties.

FIELD

This specification generally describes technology related to applications for computing devices.

BACKGROUND

Applications for computers, mobile devices, and other devices can provide useful functionality to users. Users generally provide input on user forms that are presented on user interfaces of applications. User forms can include standard graphical user interface elements such as checkboxes, radio buttons, or text fields to allow users to enter data that is sent to a server for processing. For example, a text box can enable input of a single line of text (e.g., username, password), a radio button can enable a selection from a list of items, and a submit button enables an instruction for an application to perform a specified function. Frequently, user interfaces of application are statically configured to provide pre-defined user entry forms to a user.

SUMMARY

In some implementations, a system allows customized forms to be dynamically provided through an application. The system can include an interface for an administrator to create a form, and then remotely make adjustments to the form that take effect automatically and in real time on user devices. The forms that an administrator creates can also be dynamically customized for each user. As a result, the same form definition can cause different interfaces to be shown to different users. Similarly, the same form definition can cause a different view to be shown to the same user at different times, due to differences in the context of the user. These features and others discussed below give administrators the flexibility to provide multiple variations of a form through a single form definition and easily update the form for a large number of users. Similarly, the customizations for individual users can increase user engagement with the application and reduce the burden on users to enter data in the form.

Conventional applications often do not allow remote adjustment of electronic user forms or customization for individual users. As a result, these forms have often failed to maintain consistent and meaningful engagement with users. For instance, electronic forms of applications are often defined by client-side instructions that are pre-defined for a general population of users. In the case of healthcare support applications, electronic forms that are provided to a large population of users often need to be adjusted for different users to be effective. For example, forms may need to collect different types of information at different precision levels in order to effectively monitor the individual physical and mental wellbeing across different health conditions.

In some implementations, a system is capable of variably and dynamically adjusting electronic forms provided to users on an application in order to improve collection of information related to different user-specific factors. For example, different configurations of an electronic form can be customized for users with different conditions or users with different attributes. The use of customized electronic forms can then allow for precise control over the type of data collected, techniques used to collect data, and the content provided on the customized electronic form based on user attributes. As a result, engagement between users and the application are improved by individually personalizing electronic forms provided on the application.

The server can customize the electronic forms by updating a form definition that configures the electronic form. The form definition specifies characteristics of the electronic form such as display properties, interactive elements to be included, and/or rules that vary content of the electronic form for different users or user types. The form definition can also specify different data types to be collected on the user form (e.g., user input provided on the electronic form, data obtained from third party APIs, data collected by devices wirelessly connected to the user device, or data collected by sensors of the user device). In addition, the form definition can also specify validation rules that specify types of valid or invalid input by the user.

The architecture of the system generally includes a user device that has the application installed, and an associated system where an administrator can create and update a form definition for an electronic form that is provided to the user through the application. The administrator can design the electronic form using a configuration interface that allows for customization of the electronic form by specifying data types to collect using the electronic form and/or layout parameters for displaying the electronic form on the application. An application server can then process the administrators design in order to generate a form definition that includes rules for generating the electronic form on the user device. The generated form definition is then transmitted to the user device so that the user device can dynamically generate the electronic form within the application without any intervention by the user.

The rules specified within the form definition can be used to dynamically adjust the content provided on the electronic form. A client device can interpret the form definition to adjust individual views of the electronic form, e.g., by changing the interface elements that are included within an electronic form, or adjusting the precision level of information provided on an electronic form. Adjustments can also be made to multiple electronic forms such as adjusting the arrangement of multiple forms that are displayed on a single user interface.

Adjustments to electronic forms can be carried out in real-time without requiring application updates (e.g., without altering the executable code of the application). For example, the server may periodically provide form definition updates to adjust an electronic form within the application without requiring a full application update. The application can then process the updated form definition to adjust the electronic form while the user is using the application. In this regard, the system can automatically update electronic forms responsive to data received on the user device.

If a user provides an invalid input into an electronic form, then the electronic form can be updated to restrict submission of additional information. In another example, if the application receives sensor data that reflects user performance (e.g., pedometer data), then an electronic form that requests the user to submit the number of steps may be dynamically deactivated to reduce data redundancy.

In addition, the server can adjust the form definition based on data that is received by the user device over a period of time. As an example, a form definition adjustment can include rules that specify updates for specific user activities, user behaviors, and/or user actions on the user device, and how these actions vary over time. After the server generates an initial form definition, the form definition can then be adjusted based on monitoring the user's real-time activity on the application. In this regard, adjustments can either be reactive to recent changes in a user's actions, or proactive in using pattern recognition analysis of historical user activity to anticipate subsequent changes in user activity.

In one general aspect, this specification describes a method performed by one or more computing devices. The method includes receiving, by the computing device and over a computer network, form data that specifies characteristics of an electronic form, the form data including one or more rules configured to vary the content of the electronic form that is presented for different users; obtaining, by the computing device, user data indicating characteristics or activities of a user of the computing device; selecting, by the computing device, an interactive element from among a set of multiple interactive elements based on the user data and the rules in the received form data; customizing, by the computing device, a view of the electronic form for the user of the computing device by including, in the customized view, the interactive element selected based on the user data and the rules in the received form data; and displaying, by the computing device, the view of the electronic form that is customized for the user of the computing device.

One or more implementations can include the following optional features. For example, in some implementations, the form data is configured to cause the computing device obtain (i) user input to the electronic form, and (ii) additional data from one or more additional data sources, the additional data including passively-sensed sensor data, actively-sensed sensor data, data from a sensor of the computing device, data from a device wirelessly connected to the computing device, or data from a third-party API.

In some implementations, the one or more rules include a first rule, and where the first rule specifies one or more triggers for application of the first rule, one or more conditions to evaluate for the first rule, and one or more actions to be performed based on a satisfaction of at least one of the one or more conditions.

In some implementations, the electronic form includes multiple sections displayed in a sequence, where the one or more rules customize the content of the sections or the sequence of the sections based on user input provided to the electronic form.

In some implementations, the form data defines at least one validation rule that specifies requirements for user input to a portion of the electronic form; where the method further includes: receiving an a user input through the electronic form; determining that the user input does not satisfy the at least one validation rule; and restricting submission of data through the electronic form based on determining that the user input does not satisfy the at least one validation rule.

In some implementations, the form data specifies a data type for user input collected through the electronic form; where the method further includes: selecting, by the computing system, an interactive element to receive user input of the specified data type, the interactive element being selected from among multiple different interactive elements that each receive input of the specified data type; and including, by the computing system, the selected interactive element in the customized view of the electronic form.

In some implementations, selecting the interactive element includes selecting the interactive element from among multiple different interactive elements that each receive user input of the specified data type at a different level of precision.

In some implementations, the form data is provided to an application that runs on the computing device, and the view of the electronic form is provided by the application; where the method further includes: receiving an updated form data over a network after displaying the view of the electronic form that is customized for the user of the computing device, the updated form data indicating a change to the electronic form; and displaying an updated view of the electronic form through the application in response to receiving the updated form data before restarting the application or updating executable code of the program.

In some implementations, customizing the view of the electronic form includes: determining a level of difficulty required for a user to complete data entry to the electronic form; determining that the level of difficulty exceeds a threshold level of difficulty; and in response to determining that the level of difficulty exceeds the threshold level of difficulty, adjusting the content in the customized view of the form to reduce the level of difficulty below the threshold level of difficulty.

In some implementations, customizing the view of the electronic form includes: determining that the form data instructs collection of data of a particular data type; obtaining, from the computing device, the data of the particular type based at least in part on sensor data from the computing device; based on obtaining the data of the particular type, customizing the view of the electronic form to omit a region for requesting data of the particular type from the user.

In another general aspect, this specification describes a different method is performed by one or more computers. The method includes: providing, by the one or more computers, a user interface for designing an electronic form for collecting data about a user; receiving, by the one or more computers, data indicating user input through the user interface, the user input indicating one or more data types for data to collect using the electronic form and one or more layout parameters for the electronic form; generating, by the one or more computers, form data that specifies one or more rules for customizing the electronic form; and providing, by the one or more computers, the form data to a computing device, the form data being configured to cause different versions of the electronic form to be presented to different users.

In some implementations, the method further includes: receiving, from devices of multiple users, data collected by the electronic form associated with the form data, the received data including information of a particular data type that was collected in different data formats from different users; converting the received information of the particular data type to a common data format; and storing the converted data.

In some implementations, converting the received information includes: accessing data indicating a hierarchy of categories; identifying different categories in the hierarchy that correspond to the different data formats; and converting the information of the particular data type using relationships of the categories in the hierarchy that correspond to the different data formats.

In some implementations, providing the form data to the computing device includes: providing the form data to the computing device such that the form data updates a form definition in an application installed at the computing device without any action by the user of the computing device In some implementations, the form data includes one or more state rules for the electronic form, where the one or more state rules cause the computing device to select, from among multiple assessment algorithms, a particular assessment algorithm according to data collected using the electronic form.

In some implementations, providing the user interface includes providing a user interface that indicates a set of pre-defined database fields; where receiving the data indicating the user input includes receiving data indicating selection of a particular database field; and where generating the form data includes including, in the form data, an element of the form that is personalized for a viewer of the electronic form using data for the viewer from the particular database field.

In some implementations, providing the user interface includes providing a user interface that enables a user to (i) update the form data to change characteristics of the electronic form and (ii) publish the updated form data to cause an application installed on remote computing devices to update the characteristics of the electronic form in real time.

In some implementations, the electronic form includes multiple sections shown in different views; where receiving data indicating the user input includes receiving data indicating rules configured to cause different transitions among the sections of the electronic form based on data collected by the electronic form.

In some implementations, generating the form data includes generating the form data to direct a computing device presenting the electronic form to capture data from one or more additional data sources that includes at least a device wirelessly connected to the computing device, a third-party API, and a sensor of the computing device.

In some implementations, providing the user interface includes providing a user interface that permits a user to specify one or more validation requirements for data entered into the electronic form.

Other embodiments of these aspects include corresponding systems, apparatus, and computer programs, configured to perform the actions of the methods, encoded on computer storage devices. A system of one or more computers can be so configured by virtue of software, firmware, hardware, or a combination of them installed on the system that in operation cause the system to perform the actions. One or more computer programs can be so configured by virtue having instructions that, when executed by data processing apparatus, cause the apparatus to perform the actions.

The techniques described herein can provide a number of advantages and benefits. For example, a single form definition can be provided to multiple user devices and include embedded rules. The rules may customize the display of an electronic form each time it is displayed. Similarly, the rules may allow an application to customize the form for each user and each device, so the same form definition provides significantly different presentations depending on the attributes of the user, the capabilities of the device, and/or different user inputs to the form. By maintaining and distributing form data in this manner, the storage requirements and complexity of distribution can be significantly reduced. In addition, the system can permit transmit updated form definitions to cause the forms displayed on user devices to be updated remotely and in real time or near real time. Additional advantages result from the ability to eliminate unnecessary interactions that are not likely to assist the user. By eliminating these unnecessary outputs, the user devices conserves battery power, processing cycles, and network bandwidth.

The details of one or more implementations are set forth in the accompanying drawings and the description below. Other potential features and advantages will become apparent from the description, the drawings, and the claims.

BRIEF DESCRIPTION OF THE DRAWINGS

FIG. 6 is a diagram that illustrates an example of a performance analysis report for an electronic form.

In the drawings, like reference numbers represent corresponding parts throughout.

DETAILED DESCRIPTION

Figure 1:
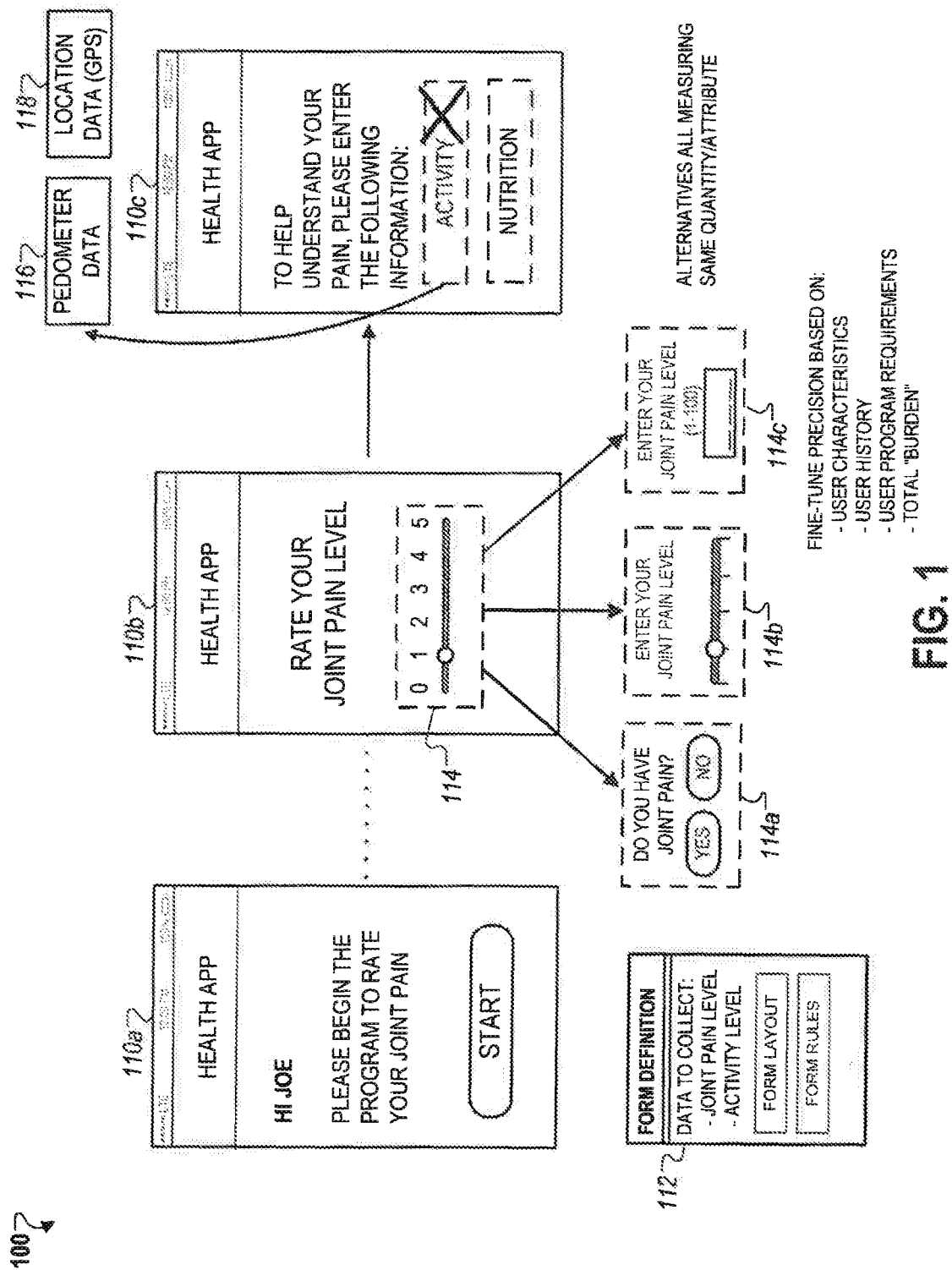
FIG. 1 is a diagram that illustrates an example of a process for dynamically generating an electronic form based on a form definition.

In general, a system allows customized forms to be dynamically provided through an application. The system can include an interface for an administrator to create a form, distribute it to various user devices, and then remotely make adjustments to the form that take effect automatically and in real time on the user devices. The forms that an administrator creates can provide a dynamically customized view for each user. As a result, the same form definition can cause different interfaces to be shown to different users. Similarly, the same form definition can cause a different view to be shown to the same user at different times, due to differences in the context of the user. These features and others discussed below give administrators the flexibility to provide multiple variations of a form through a single form definition and easily update the form for a large number of users. Similarly, the customizations for individual users can increase user engagement with the application and reduce the burden on users to enter data in the form.

As described throughout, form definitions can be used to configure and adjust an electronic form provided by the application. The form definition is initially specified by a system administrator on a configuration interface that allows the administrator to customize, for example, data types to collect using the electronic form and/or layout parameters for the electronic form. The specified form definition is then transmitted to the user device to either dynamically generate or adjust the electronic form of the application without any intervention by the user.

The architecture of the system provides various improvements in dynamically configuring an application to provide customized electronic forms to individual users, which often requires significant computing and storage resources on client devices. For example, in order to generate a new electronic form to be displayed on an application, a software update for the entire application is usually necessary because form data is often pre-configured within application code. The architecture of the present system, however, utilizes configurable form definitions that process a set of rules that dynamically configures an electronic form based on data collected on the application. For instance, the client device may process form definition data to generate multiple customized electronic forms without requiring an application-wide update from the server. As described below, this enables the application to utilize less storage space on the client device and less network bandwidth since the entire application does not require an update each time a new version of an electronic form is to be generated.

In addition, the architecture of the system enables the system to address various problems that arise in the networked environment of client-based applications. As an example, application configurations provided by servers are often static for significant periods of time and may require major updates to application code. This can be time consuming for application developers and end-users since it requires periodic manual reconfiguration of applications, and periodic delivery of the reconfigured applications. As described in more detail below, the architecture of the system addresses this problem by, among other techniques, employing the use of form definition data that uses a collection rules to automatically adjust electronic forms to be provided on an application without requiring changes to the entire application configuration. This enables an administrator or a developer to adjust the information collected by the application with limited intervention. Moreover, processing of these rules by the system can automatically and dynamically alter a user's experience with the application without requiring users to manually download application updates.

Further, the implementations discussed below can provide ongoing customization of user experiences in an efficient manner, reducing computation needs, power consumption, and other resource requirements. Processing rules within form definition data for a large set of users can be done efficiently by limiting processing of rules for a given user to a particular subset of rules applicable to the user. Even for rules in the subset, processing can be limited by using the trigger as a threshold test, so that further processing of the rule is not performed until and unless the trigger is detected.

Another problem that often arises in networked environments is that applications are often unable to provide effective real-time adjustments that are appropriate for a user's particular circumstances. For example, while some applications can process historical data and provide analyses and recommendations, such applications are often unable to dynamically adjust (i) the content that is provided to the user on the application, and (ii) the arrangement specifications of the application (e.g., types and characteristics of interface elements, color schemes used in style specifications, etc.) without requiring a manual application update. As described in more detail below, the architecture of the system can address this problem with, among other techniques, the use of a collection of rules that associate triggers and conditions with actions to be executed by the system. The scope of each rule can be manipulated based on selections of the triggers, conditions, and system actions specified by an administrator. In this regard, some rules can be applied to make general adjustments (e.g., providing notification badges, or adjusting content provided), whereas other rules can be applied as context-specific changes that respond to user behavior.

Yet another problem that often arises in networked environments is that third-party organizations that create content to be provided on an application developed by a separate entity often have limited ability to control as to how a user interacts with their content. For example, third-party organizations often have to adjust content creation to satisfy application requirements set forth by application developers that provide updates to an application. As described in more detail below, the architecture of the system can address this problem, by providing a configuration interface to an administrator associated with a third-party organization that enables the customization of forms to be provided in third-party application modules accessible on the application by a user. The configuration interface enables the administrators to make adjustments using a user-friendly interface rather than having to adjust the application code directly. In addition, because the system architecture enables the creation of multiple third-party application modules to be provided within the same application, different third-party organizations can configure and adjust the content to be displayed within their respective application modules.

FIG. 1 is a diagram that illustrates an example of a process 100 for dynamically generating an electronic form based on a form definition. The form generation techniques described in this document can be used for any appropriate application. For clarity in illustration, examples of forms related to healthcare management are provided and discussed, but the technology is not limited to those uses or data types.

In the example depicted in FIG. 1, a health application on a user device is used to periodically monitor joint pain experienced by a user of the user device in relation to activity level of the user. The health application accesses a form definition 112 that describes characteristics of an electronic form to collect data about the user. The form definition 112 includes information that allows the application to provide user interfaces that request certain data from the user. The form definition 112 can also cause the application to obtain other information about the user, for example, actively-sensed sensor data, passively-sensed sensor data, information through third-party application programming interfaces (APIs), and so on. Based on the form definition 112, the application in the example of FIG. 1 provides user surveys for the user to provide input about pain levels experienced by the user. The user surveys include different views or user interfaces that accept user input. Input received on the electronic forms can then be collected, analyzed, sent to a server system, and used by the application to assist the user.

The user is initially directed to a start a user survey on an interface 110a. Upon receiving a user input to initiate the survey, the system dynamically generates a user interface 110b that includes a form element 114 to enable the user to rate a joint pain level. The form element 114 is generated based on a configuration specified by the form definition 112. For example, the form definition 112 may specify a type of data to be gathered, such as joint pain level, and may also specify layout parameters about how the user interface 110b should appear. In addition, the application can customize one or more elements of the user interface 110b for the specific user. In some instances, the form definition 112 itself describes different variations of an interface that can be provided through rules embedded in the form definition 112. In addition, or as an alternative, the application that generates a view of the form may apply customizations that are not specifically indicated by the form definition 112.

In the user interface 110b, the application determines which of several form elements 114a, 114b, or 114c to display based on a set of rules governing the configuration of the electronic form. Each of the form elements 114a, 114b, or 114c can be used to obtain data about a joint pain level. However, the different form elements 114a, 114b, or 114c obtain the information at a different level of precision, and different elements may be appropriate for different users. The form element 114a represents an example of a low-precision element that only accepts binary input from the user (e.g., "Yes" for experiencing joint paint or "No" for not experiencing joint paint). The form element 114b represents a medium-precision element with a slider element that allows a user to specify a value within a finite spectrum of values (e.g., a value along a range as illustrated in FIG. 1). The form element 114c represents a high-precision element that allows the user to provide a numerical value within a specified integer range (e.g., 0 to 100).

The application may select one of the electronic form elements 114a-114c to display on the interface 110b based on rules specified by the form definition 112. The form definition 112 may specify various rules that specify a selection of a particular visual format based on user characteristics, user history, requirements for a health program that the user participates in (e.g., program objectives, milestones, etc.), and a total burden imposed on the user, and other factors. As an example, a user profile may indicate that the user has previously had difficulty answering questions on electronic surveys, or that the user had a low rate of completing surveys. The form definition 112 may specify that for users with low completion rates, the form element 114a should be selected since this form has the lowest complexity with a binary selection. In another example, the user history may indicate that a user's joint pain level, indicated by the previous user inputs, has varied greatly. The form definition may specify that if the variation in prior inputs exceeds a certain level, then the form element 114c should be selected to provide the user with greater precision in providing a pain assessment. In other examples, the selection may also be based on user preferences, the type of medical condition monitored for the user, among other factors.

When customizing a user interface for a user, the application may apply any of a variety of rules. Some rules may be general or default rules, such as an application-level rule that attempts to maintain a consistent visual style or to keep the complexity of a form below a maximum level. Other rules may be specific to individual forms, as indicated in specific form definitions. The form-level rules may be used in addition to the general rules, and may override the general rules for the purposes of presenting specific forms.

A variety of customizations can be made to personalize a view of an electronic form for a particular user. For example, the application can also determine whether or not to request certain information from a user. Based on the data available, or information about the current context of the user, the application may omit certain form elements from the user survey. This determination can be based on different types of data that are received by the application. For example, an application can obtain data from sources other than user input, such as sensor data or stored data from the user's device. This additional data can be used to meet the data collection requirements indicated by the form definition 112, and can also adjust the view of the form.

In FIG. 1, the application receives pedometer data 116 indicating the user's current number of steps taken and location data 118 indicating the user's current location. The form definition 112 may direct the application to provide an interface to collect activity data and nutrition data from the user. However, the application can determine that the pedometer data 116 provides the activity level information needed, and so the user does not need to enter input. Because the pedometer data 116 already indicates the activity level of the user, the application no longer requires user input to identify a measured activity level. The application generates the user interface 110c to exclude the "activity level" form element, thus simplifying the view shown to the user. In this regard, data received from external sources (e.g., wearable devices wirelessly connected to the user device, third party application package interfaces (APIs), and sensors of the user device) can be used to dynamically generate electronic forms to minimize unnecessary user input. If the pedometer data 116 or other data were not available to the application, then a different user interface including a request for activity level data would be provided. The form definition 112, may indicate that the application should acquire information from certain data sources. In addition, or as an alternative, the form definition 112 may indicate certain types of data to acquire, and the application may include data separate from the form definition 112 that specifies sources from which to acquire that data, such as a mapping between data types and data sources.

As shown in FIG. 1, a single form definition 112 can define the characteristics of multiple user interfaces 110a-110c. Together, these user interfaces 110a-110c can provide a multi-stage form with multiple views presented sequentially. According to the rules in the form definition 112, the content of each individual view, the sequence of the views, and whether certain views will be shown to a user can vary from one user to the next. Similarly, the rules in the same form definition 112 may cause differing views to be provided to the same user at different times.

As described throughout, rules embedded within the form definition can be used to customize an electronic form for a particular user. Each rule can be associated with one or more triggers, one or more evaluation conditions, and one or more specified actions to be automatically performed by the system. Satisfaction of the triggers of a rule can be used to automatically initiate an evaluation of associated conditions of that rule. The system then performs the corresponding system actions in response to determining that at least one of the conditions has been satisfied. The embedded rules can thus be used by an application to determine, for example, which of multiple forms should be provided, when a form should be displayed, the content and appearance of a form, which data should be requested through a form, what level of precision or complexity should be used in the form, and other form characteristics. Some embedded rules may be used generally to select or schedule a form for display, while other rules may be used specifically to customize a form for an individual user. This technique can be used selectively perform system actions related to the electronic form based on the triggers and conditions specified by individual rules within a repository of rules.

The repository of rules may include different types of rules that adjust form generation in various ways. For instance, the individual rules within the repository of rules can vary in scope and in hierarchy to enable an application to adjustably generate an electronic form. As an example, certain rules can be "state rules," which enable the system to select an appropriate assessment algorithm from among multiple assessment algorithms based on the data collected using an electronic form. In this example, each state rule may specify the use of a different assessment algorithm as a system action based on the satisfactions of different triggers and/or conditions. In another example, other rules can be "validation rules," which enable the system to determine whether a user input on the electronic form is valid based on the data type associated with the conditions specified by each validation rule. While state rules and validation rules are two examples of different types of rules, other examples are also possible.

State rules can be defined in any of various ways. As an example, a state rule can have one or more triggers organized in an unordered list. If any of the specified triggers occurs, the state rule is executed. Similarly, a state rule can have one or more conditions organized in an ordered list. The conditions can be evaluated in sequence, until the one of the condition expressions evaluates to "true," indicating that the condition is satisfied. The application can then cause the action associated with the satisfied condition to be performed. Each condition may have a single condition expression. In some instances, a condition can have a "null" value or "true" value indicating that the condition is always satisfied and always evaluates to true. For each condition, one or more actions are defined. These actions can be organized in an ordered list or be prioritized in another manner. When a condition is selected as being satisfied (e.g., is the first in an ordered list that evaluates to true), each of the actions will be performed, in the sequence defined by ordered list of actions.

Other variations of state rules can be used. For example, in some implementations, certain actions may have additional conditions that must additionally be satisfied before the action is performed. As another example, some state rules may be defined so that each condition is evaluated after a trigger is detected, and the actions specified for each condition that is satisfied can be performed. In some instances, actions may set, clear, or adjust values for parameters of a form being displayed. The actions may change various display configuration properties. The various values or properties can be specified by a type, an identifier, and/or a path through the hierarchy of elements specified in the form data.

As described throughout, a customized electronic form can be used for different types of health management applications. For example, in some implementations, form customization enables the system to provide risk assessment forms that provide directed questions to obtain information about a user's present health condition. The information obtained through the customized electronic form can then be used to evaluate health risks associated with a known medical condition of the user. The types of customized forms can typically be used to improve a user's progress through a particular health module. In another example, form customization enables the system to obtain user feedback data on the effectiveness of the actual health module. For instance, electronic forms can be provided to request a user's feedback on a treatment programs specified by a health module they are presently participating in. The two examples above illustrate that form customization can be used to both gain information relating to a user's performance within a health program, as well as the effectiveness of the health program. The obtained information can be enable an administrator to identify changes to either a user's individual treatment plan (e.g., an adjustment of individual user's goals or actions), or changes to the way in which a health program is provided to a collection of users (e.g., adjusting a care plan for users that are diagnosed with the same medical condition).

Figure 2:
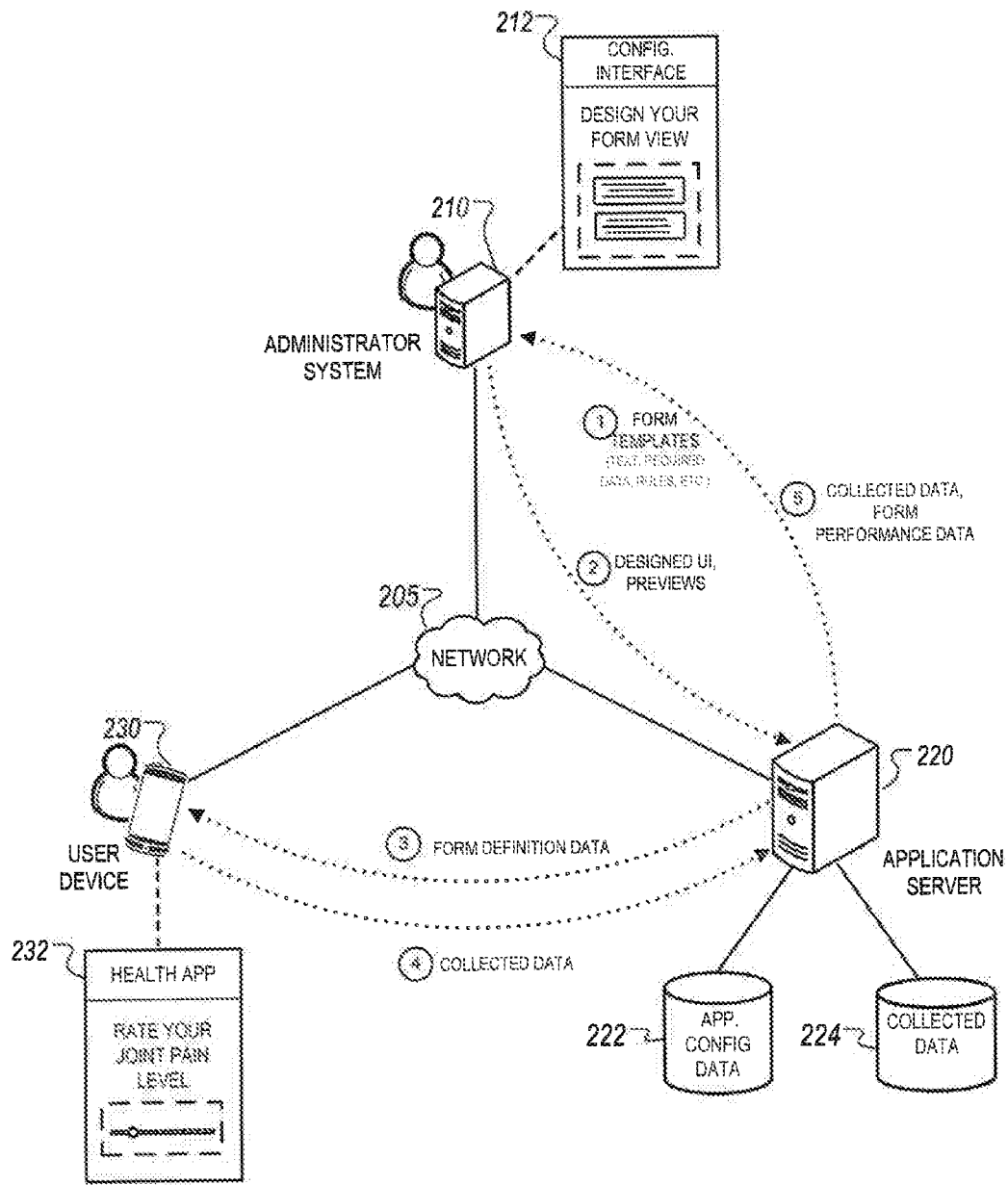
FIG. 2 is a diagram that illustrates an example of a system that is capable of generating dynamic electronic forms.

FIG. 2 is a diagram that illustrates an example of a system 200 that is capable of generating dynamic electronic forms. The system 200 generally includes an administrator system 210, an application server 220, and a user device 230 connected over a network 205. The administrator system 210 provides a configuration interface 212 that allows an administrator to design electronic forms that are provided for output on an application 232 running on the user device 230. As described above, the system 200 enables data exchange between the administrator system 210, the application server 220, and the user device 230 such that electronic forms displayed on the applications 232 can be dynamically constructed and adjusted based on forms designed by the administrator using the configuration interface 212.

In general, the application 232 can support multiple program modules provided by different third-party organizations separate from the organization associated with the application server 220. The various program modules can include health modules. A health module can represent any type of program to measure, maintain, or enhance a person's physical and/or mental wellbeing. Health programs can be used for monitoring, treatment, research, coaching, teaching, and other purposes. Each program can provide a user experience that benefits the user through the use of the application. A user can enroll in multiple health modules within the application 232 that are provided by different organizations. In this regard, the system 200 enables administrators from different organizations to design customized electronic forms that are provided within different programs of the same application.

In step (1), the administrator system 210 initially receives form design data from the application server 220. As noted above, the administrator system 210 can be a client device of a third-party administrator that creates or maintains a program provided through the application server 220. The design data may include pre-generated form design templates that specify text, required text, and/or associated rules. The design templates may be specified by a particular medical condition, a particular health program in which a group of users have participated in, or an entity or organization that provides healthcare services to a group of patients. For example, design templates for an employer may include form data that relates to specific health programs or initiatives supported by the employer. In another example, design templates for a particular medical condition may include form data for collecting patient information in relation to treatment of the particular medical condition.

The administrator may then use the configuration interface 212 to design customized electronic forms to be provided for output on the application 232. The customized electronic forms may include a customized selection of interface elements, content to be provided to the users, and different data types to be collected on the electronic forms. More specific descriptions related to the configuration application are provided below with respect to FIG. 3.

The administrator to configure many permutations of form experiences with a single form definition. This allows for a high degree of personalization and engagement tailored for individual users. Depending on the choices that a particular user makes when viewing the form, and the data that is entered in the form, the appearance and behavior may change. For example, the state rules discussed above can define different combinations of content and input fields to display, depending on the user's responses and other user information obtained from other sources besides the input fields of the form. In some implementations, an administrator may define a set of rules that provide a condition-based survey with branching logic or cascading user input fields, where the entry in first field governs the presentation of a second field in the form.

In step (2), the customized electronic forms designed by the administrator are then transmitted to the application server 220. The customized electronic forms may include designed user interfaces that include the customized electronic forms, rules that indicate the behavior of forms or variations of the forms for different users or scenarios, or various types of instructions that cause the application 232 to display the customized forms on the application 232. The data received from the administrator system 210 may then be aggregated and packaged by the application server 220 based on a set of stored application configuration data 222.

In step (3), the packaged data can then be transmitted from the application server 220 to the user device 230 as form data that configures the application 232 to provide the customized electronic forms designed by the administrator for display to the user. The updated definitions in the form data are provided automatically and remotely to the user devices, substantially in real time. In some implementations, when the form data for a program module is updated, the packaged data can be pushed to each user device associated with a user who has subscribed to that program module. In some implementations, the application on the user device periodically requests updates to form data for the programs that are subscribed.

The dissemination of form data to the user devices requires no action on the part of the subscriber, e.g., there is no need for application updates, re-login to an application, or even restarting of the application. Once form data is received at a user device, a new or updated form can be provided as soon as display of the form is triggered according to the rules in the form data.

This ability to almost instantly provide form updates also assists administrators to preview and test form configurations. The administrator may cause the an updated form definition to first be provided only to certain devices designated for testing, or to be active on only certain devices. This limited distribution phase allows an administrator to see the results of updated forms, on the actual types of devices where the forms will be seen, before disseminating the updated form to subscribers. With these techniques, administrators can conduct rapid prototyping of forms for user experience and usability testing. For example, form updates can be rolled out to small groups, assessed, updated, and then provided to a broader set of users.

The form data can include form definitions that allow user devices that receive the form data to customize views of the forms for specific users, as described above, and rules that specify triggers and conditions in which the customized forms are provided for display to the user.

In some instances, the form data may also include instructions that cause the user device 230 to obtain information through the user input of the customized electronic forms, through other devices that are wireless connected to the user device 230 (e.g., wearable devices), third party application package interfaces (APIs), or sensors of the user device 230. For health-related forms, this allows a single form to collect objective, un-biased information about a user in addition to self-reported data obtained as user input to the form. In other instances, the form data may include specifications that configure or adjust the content of the customized forms, or the arrangement of customized forms on the interface of the application 232. For example, the form data may specify multiple sections for a particular electronic form, and rules included within the form data may customize the content of each section or the sequence of the sections based on user input provided on the electronic form.

In some implementations, the sections of a form can be nested. For example, the form data may specify different views or portions of a form, and groupings or other relationships of the different views. For example, form data may specify that different sections of a form should be shown, depending on a user's responses to a first section of a form. For example, an initial view of a form may ask a user to input information about exercise. The form data may specify that if the user enters a type of exercise that is typical for that user, then the form should then proceed to display the next section, e.g., asking about nutrition. The form data may specify that if the user enters a type of exercise that is new for the user, one or more nested sections related to exercise should be provided, e.g., congratulating the user for trying something new, asking about how the user liked the new activity, and so on. The form data may organize form sections into groups or hierarchies that specify different nested elements that are selectively displayed according to the current information about the user. Different views can be displayed in sequence as indicated by the form data.

In other examples, the form data may define validation rules that specify requirements for user input to portions of the customized electronic forms. For instance, the form data may specify a specific data type for a particular electronic form (e.g., numerical input, or input in a particular numerical range). The form data may include instructions to adjust the configuration of the customized form in response to determining that a user's input is invalid or does not satisfy the requirements set forth by the validation rules. As an example, an electronic form for physical pain level measurement may request that a user may provide a description of the pain experienced by the user. In this example, a validation rule may indicate common terms that are related to physical pain measurement, which would represent acceptable input in a free-form text input area. Inputs that do not satisfy the criteria in the validation rules, such as a user input relating to depression (e.g., emotional pain), can be identified as inappropriate. In this instance, the user may have misunderstood the question presented on the initial form. In response to detecting the inappropriate input, the application 232 may prompt the user to correct the answer, or may prevent the user from continuing or submitting the form.

In step (4), data collected by the application 232 through forms is provided to the application server 220. The collected data 224 can include user input (e.g., data indicating user responses or interactions with a view of the form) as well as other information that a form definition directs the application 232 to obtain. The application 232 may periodically collect user input data provided to the customized electronic forms (e.g., text submitted, user selections from a list of presented options, etc.) and other input data that is associated with the user's participation in the electronic form (e.g., total time taken to complete the electronic form, other background applications used by the user while completing the electronic form, etc.). The application 232 may also collect other data separate from user input, as directed by the form definition. For example, the application 232 may collect passively-sensed sensor data or actively-sensed sensor data. The data can be obtained from additional data sources such as the sensors of the user device 230, a wearable device wirelessly connected to the user device 230 (e.g., through Bluetooth), or from a third-party API. The collected data for each electronic form is then transmitted to the application server 220 for storage and analysis.

In step (5), the application server 220 then generates performance reports for the customized electronic forms based on the user input data collected on the application 232. The performance reports may include summary information indicating user patterns while completing the customized electronic forms (e.g., amount of time spent on the customized electronic forms), or analytical determinations based on the user patterns (e.g., effectiveness of the customized electronic forms). More particular descriptions related to the performance reports that are generated for the customized electronic forms are provided below with respect to FIG. 6.

The performance reports generated by the application server 220 are then transmitted to the administrator system 210 for analysis. In some instances, the performance reports may be used to adjust form definitions for customized electronic forms in order to improve the engagement of the user on the customized electronic forms. Adjustments to the electronic forms may be made manually by the administrator on the configuration interface 212, or automatically by either the administrator system 210 or the application server 220 based on the information indicated by the performance reports. In the first example, the administrator can adjust the form definition by providing input on the configuration interface 212 (e.g., adding or removing interface elements of an existing form definition, adjusting the content to be displayed, etc.). In the second example, automatic adjustments to the form definitions can be processed based on the identification of specific types of user input data (e.g., not receiving any user input on a particular electronic form for a long period of time, indicating that it may no longer be relevant to the user). In addition, as described above, adjustments can be processed in real-time such that an existing electronic form may be adjusted as the user is providing user input on the electronic form.

In some implementations, the administrator can use the configuration interface 212 to configure an entire health risk assessment (HRA) for the user. The HRA can evaluate health assessments and recommendations based on data collected through the application 232 (e.g., passively or actively sensed data, data obtained from third-party APIs, etc.) in addition to self-reported user input data on the electronic form. Because the configuration interface 212 enables the creation of different types of electronic forms, the administrator may configure different HRA forms for a single health module that is run within the application 232. A health module can represent any type of periodic monitoring or treatment program that the user can participate in through the use of the application. For example, a user can enroll in multiple health modules within the application 232. In addition, the administrator can configure form definitions to specify rules that direct the selection of different HRAs based on the data collected on the application 232.

In other implementations, other types of clinical assessments can be incorporated into the content of the electronic forms. For example, the administrator may configure clinical outcome assessments (COA), patient reported outcomes (PRO), among other types. As described above, rules specified within the form definition can be utilized to provide specific types of output in response to receiving different types of user data. In this regard, the administrator can customize the electronic form to the specific needs of a particular healthcare provider or entity in order to perform a large variety of patient monitoring functions.

In some implementations, the administrator can also use the configuration interface 212 to configure an entire diagnostic tool (EDT) with the use of customized electronic forms. For instance, the administrator may create a diagnostic form with a form definition that specifies rules for predicting a diagnosis for a user based on input provided on the user. As described above, the particular diagnostic evaluation applied can be varied based on the different types of data collected on the diagnostic form.

In other implementations, the administrator can configure automated clinical decision support features into the electronic forms using the form definitions configured on the configuration interface 212. For example, the configured form definition can include rules that automatically provide clinical recommendations for display on the electronic form based on the contents of the data collected by the user. The rules can associate different types of input data that are associated with particular medical conditions with the corresponding clinical recommendations that are often provided as solutions to types of symptoms experienced by the user. As an example, if a user submits on the electronic form that he/she is experiencing pain, a rule can be configured to automatically provide a recommendation to take a pain relieving medication in response to receiving the user input.

Figure 3:
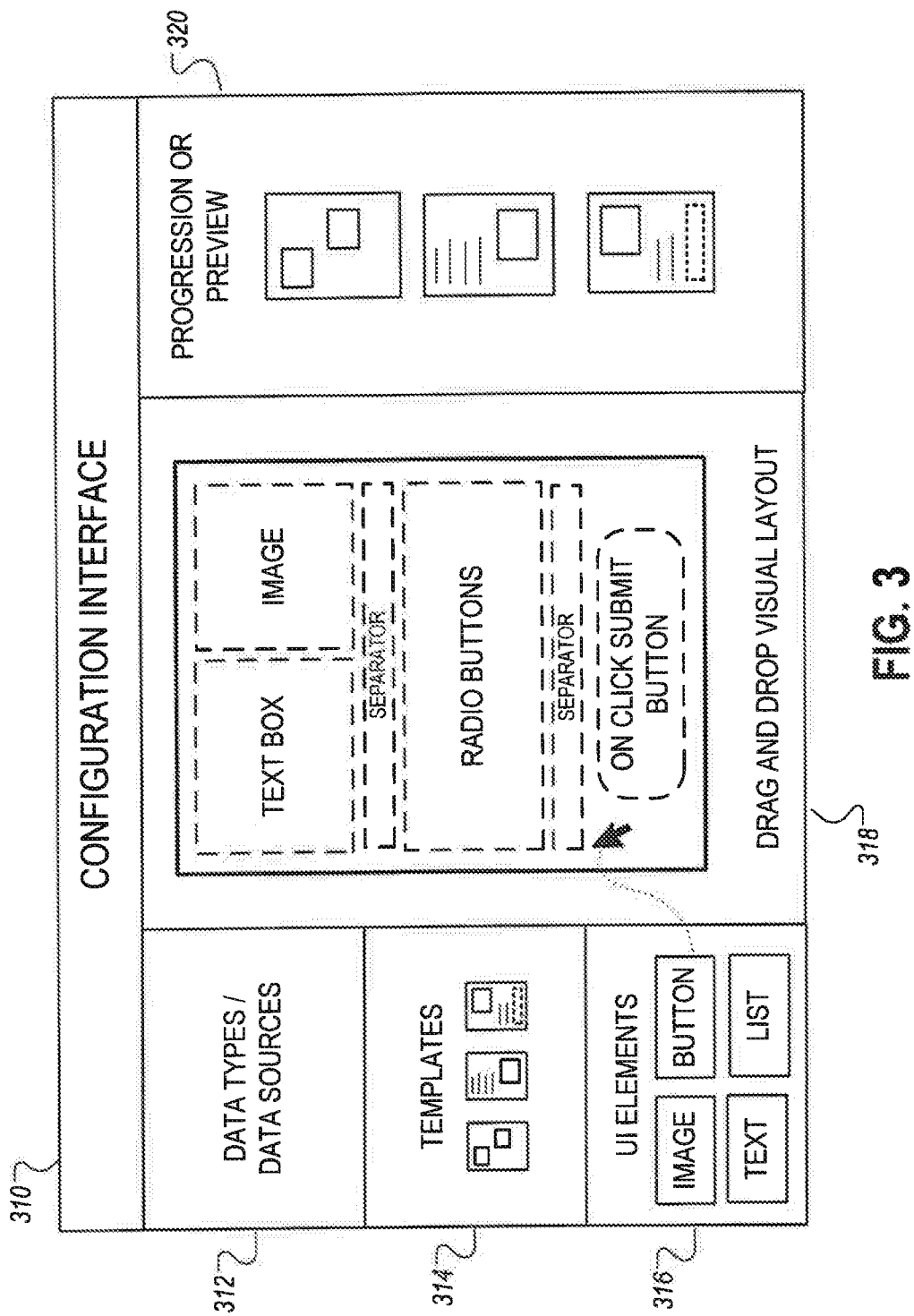
FIG. 3 is a diagram that illustrates an example of a configuration interface for customizing form definitions.

FIG. 3 is a diagram that illustrates an example of a configuration interface 310 for customizing form definitions for electronic forms. The interface 310 may be presented to the administrator on the configuration interface 212 described above. The interface 310 allows an administrator to have fine-tuned control over various aspects of an electronic form. For instance, in region 312, the administrator may select a data type for the user input to be received on the electronic form (e.g., text input, voice input, etc.), and a data source for the user input to be received on the electronic from (e.g., user input data received through the keyboard of the user device 230, input data received from other devices wirelessly connected to the user device 230, input data received from third party APIs, input data received from sensors of the user device 230). In some instances, the administrator may also specify whether the input data to be collected is passively sensed data, actively sensed data, or a combination of both.

In region 314, the administrator may select from among a set of pre-generated templates for the electronic form. The pre-generated templates may be obtained from prior configurations of other customized electronic forms that are stored locally on the administrator system 210, or other configurations that are stored remotely on the application server 220, e.g., configurations made by other users. As an example, the administrator may select a form template from a repository of form templates that categorizes the templates across various categories (e.g., health program, affiliated entities/organizations, associated medical conditions, etc.). After importing a form template, the administrator may also make additional updates to customize the electronic form that is being designed. For example, an administrator may begin with a standard template to quickly obtain a functional form for acquiring data of a needed type. The administrator may then customize the appearance and behavior of the form, e.g., selecting the color scheme, logos, and other information. In this manner, the administrator can quickly design an entire form, with appropriate customized branding to set it apart from others available through the application 232, without writing any computer code.

In region 316, the administrator may select the user interface elements to be included within the electronic form to be designed. For example, the administrator may include images, buttons, text boxes, lists, and radio buttons, among other types of common interface elements. The administrator may also specify ways in which the user interacts with each interface element. For example, the administrator may configure rules that adjust the availability of certain interface elements based on the satisfaction of specified triggers or conditions associated with the interface element. As an example, a particular interface element may only be available once the user has provided a valid user input to a preceding user interface element within the electronic form.

In region 318, the administrator may adjust the arrangement of interface elements and/or the interaction rules of interface elements within the electronic template through a drag and drop visual layout. For example, as depicted in FIG. 3, the administrator can configure locations in the electronic form where the selected user interface elements should be placed, specify field values for certain elements, or provide interactive elements that helps the user transition between different parts of the same electronic form, or different electronic forms. In some instances, the administrator may also specify embedded conditional logic into interface elements for performed pre-determined calculations based on the user input provided on other interface elements (e.g., calculating a body mass index based on the mass and height submitted by the user on two preceding fields).

In region 320, the administrator may adjust the presentation of the electronic form. For example, the administrator may adjust the size of interface elements, colors of the interface elements, fonts of text to be displayed, and/or other graphical attributes associated with the interface elements (e.g., shadows, line thickness, padding, margins, orientation, etc.). An administrator may also adjust the timing associated with when the electronic forms are provided on the application. For example, the administrator may adjust time delays between a designated user input that initiates a display of an electronic form, specify triggered events that either cause an electronic form to be displayed or removed from display, among other types of settings.

The configuration interface 310 may additionally include a progression or preview tab that enables the administrator to view progressive changes made to the draft electronic form (e.g., history of changes made from a pre-existing template) and/or a preview of electronic form within the user interface of the application 232.

The administrator may specify various user-specific customizations that should occur. For example, the configuration interface 310 may provide a list of database fields from which data may be obtained at the time of form presentation. These fields may represent characteristics that can be obtained from a user profile, e.g., a field [Subscriber_Name] or [Subscriber_Profile_Image]. When a view of the form is generated, the application 232 obtains the current information from the user's profile, or other data source referenced, to generate a custom view of the form. The database fields may also provide information that helps motivate and engage a user. For example, the form could include a sentence such as "[Supporter] thinks it's important for your cancer treatment to complete this survey," where the [Supporter] field is replaced by a name of friend of note from that person could also be obtained and presented in the view of the form.

The present techniques can facilitate efficiently and effectively conducting large-scale data collection projects through surveys. Other systems that use hard-coded forms often lack the flexibility to control to edit the survey or add new survey questions after deployment. With the techniques disclosed herein, a versioning technique can be used to allow multiple versions of a form. When the administrator edits an existing data collection form, validation rules automatically determine whether there are a subscriber has utilized this form to submit data. If not, then the form is edited and saved as the same form version in the database. If a user has submitted the form previously, then a new version of the form is automatically saved. Any subscriber presented with the form will automatically be presented with the newer version of the form. However, if an existing subscriber edits or views a form that they saved using the older version, the system correctly presents the older version of the form. This allows seamless updates for users that have not yet used a form, while preserving the entered data and progress of users who have invested time in filling out the form already. This solves a business problem for large survey projects, which frequently need updates and additions. As a result, a correction to a spelling error, rephrasing a question, or adding sections to a survey can be done easily by a remove administrator for all users. The administrator simply edits the form and it is automatically enabled for anyone already using the administrator's module through the application 232.

Figure 4:
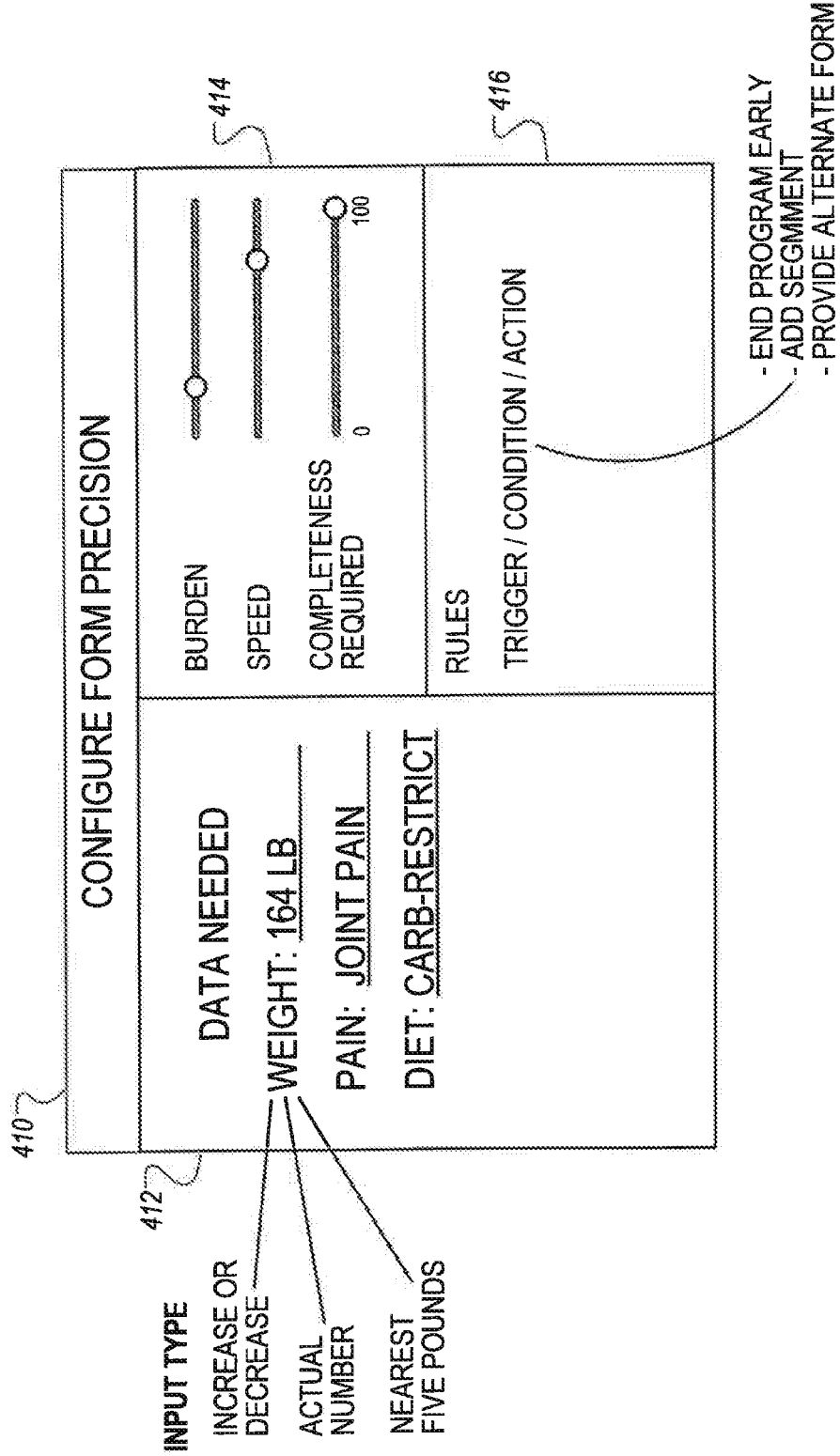
FIG. 4 is a diagram that illustrates an example of a configuration interface for customizing precision levels for data to be collected on an electronic form.

FIG. 4 is a diagram that illustrates an example of a configuration interface 410 for customizing precision levels for data to be collected on an electronic form. The configuration interface 410 enables the administrator to configure different precision levels of information shown on a customized electronic form. As described previously with respect to FIG. 1, such configurations can be used to cause the customized electronic form to dynamically adjust to one of the specified precision levels as the user is interacting with the electronic form.

In the example depicted, the configuration interface 410 allows the administrator to specify the data that is requested from the user (e.g., weight, pain, diet information). In region 410, the administrator can specify the level of precision for the information requested on the electronic form. For example, the electronic form may request an increase or decrease in weight, the actual number corresponding to the user's weight, or an estimate of the user's weight to the nearest pounds.

In region 414, the administrator may specify a set of requirements that customize the electronic form for a particular user or a particular group of users. For example, an administrator may specify a target level for the burden imposed on the user (e.g., the difficulty for the user in providing the information requested on the electronic form). As another example, the administrator may indicate a target level for a completion speed (e.g., the time it takes for the user to complete the electronic form), and a requirement for how complete responses need to be in order to be considered a satisfactory or valid user input.

The set of requirements provided on the configuration interface 410 may then be used to automatically and dynamically configure and adjust the electronic form on the application 232 based on data associated with the user. Because the requirements are different for each user, the application 232 may variably adjust the electronic form based on the data associated with each individual user. For example, an administrator may use the configuration interface 410 to create an electronic form with a "low burden" requirement. When the electronic form is generated on the application 232, the low burden requirement for a younger user may be higher than the low burden requirement for an older user with disabilities or potential memory loss. Thus, in this example, the application 232 may use demographic information associated with the user to variably construct a similarly configured electronic form to provide different user experiences.

In region 416, the administrator can configure specific rules that coordinate the configuration and/or adjustment of an electronic form in relation to specified triggers and conditions associated with the electronic form. For example, the configuration interface 410 may provide a drop-down list that allows the administrator to select from a list of triggers and a list of conditions. Examples of triggers include receiving sensor data indicating that the user has recently fallen, receiving user input data indicating an abnormally high pain level measurement, and/or data from a wearable device indicating insufficient physical activity. Examples of conditions may include determining that the user's historical activity pattern is below an anticipated goal specified by a treatment program, data indicating that the user has failed to sufficiently complete the last four electronic forms, among others.

The administrator can then specify actions to be performed by the application 232 in response to a satisfaction of the triggers and/or the conditions. The administrator can either specify application-specific actions (e.g., ending a program early), or actions to be performed in relation to a particular electronic form (e.g., adding a new segment to the electronic form, providing an alternative form, etc.). In this regard, the associated rules of the electronic form can be used to dynamically adjust the content provided on the electronic form and/or the presentation of the electronic form in relation to present conditions associated with the user based on recent data received on the application 232.

The application 232 may customize the content and appearance of a form for a particular user based on, for example, a language or dialect of the user, a reading level of the user, a health literacy of the user, impairments of the user (color blindness, etc.), a technology fluency of the user, operating system conventions, a current context of the user or the user device, and other factors. For example, the application 232 may store, or access from the application server 220, a user profile for the user to obtain scores for any or all of the factors indicated above. The application 232 may use the scores for these user-specific factors to apply rules embedded in the received form definitions. A form definition may include a rule that selects among different text prompts to provide based on a language of the user and a reading level of the user, thus providing an understandable instruction to each user despite the widely varying characteristics among the user base. The application 232 itself may apply general rules separate from form definitions, for example, to adjust form appearance according to user preferences in the application 232, to adjust form presentation for the characteristics of a user device (e.g., screen size, resolution, etc.), to select content that is in the user's language, and so on. Additional changes that can be made, based on rules in form definitions or by the application 232, include presenting text in the user's language, setting different font sizes depending on a user's age, phrasing questions differently depending on the user's gender, and phrasing questions differently depending on a user's age and/or reading level. A form definition may provide multiple different variations, such as multiple phrasings of a question, with rules indicating when each version is appropriate. The application 232 applies those rules to select and present the content most appropriate for the user each time a view of the form is displayed.

Figure 5:
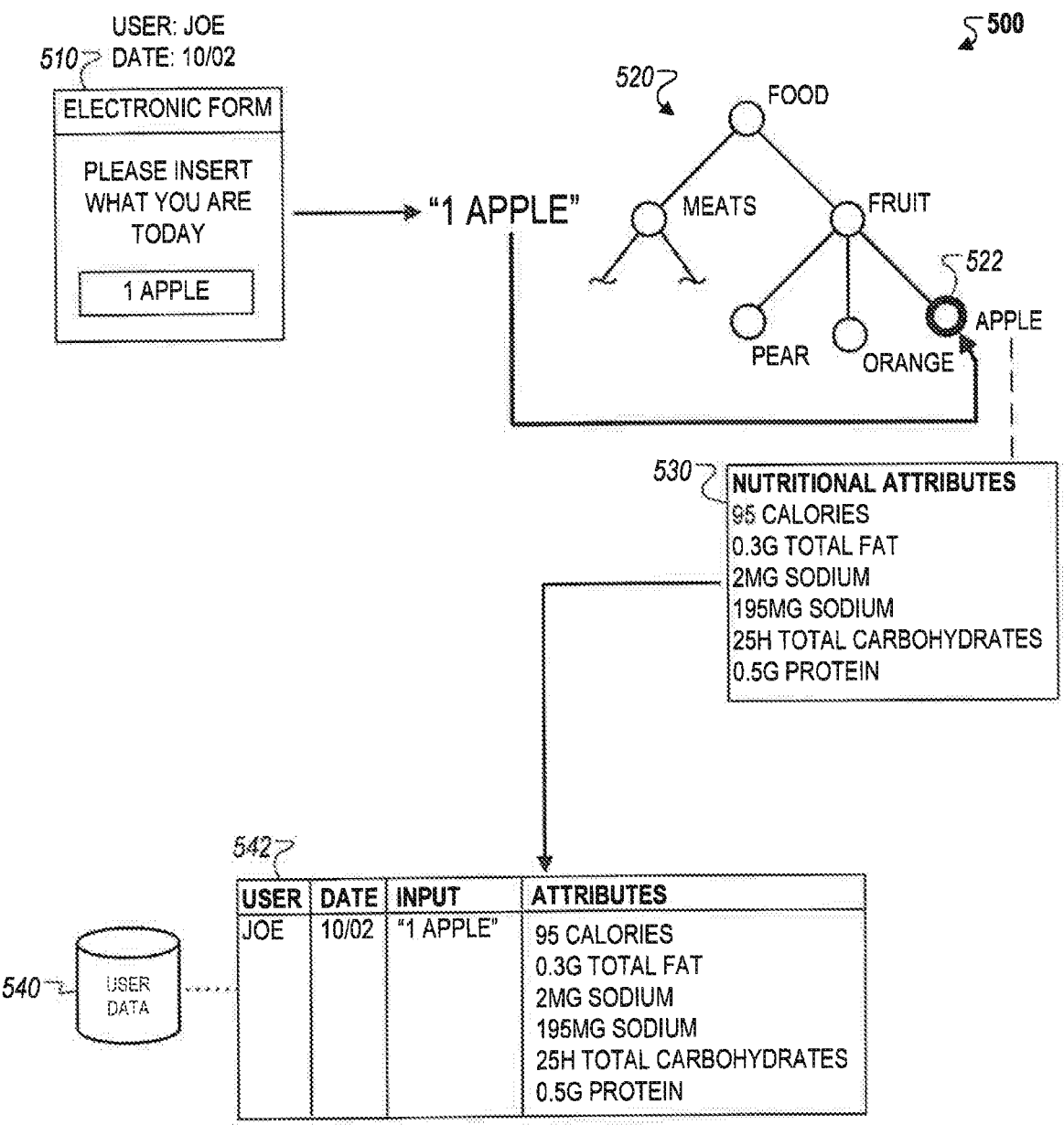
FIG. 5 is a diagram that illustrates an example of a process for processing user input on an electronic form in relation to a set of hierarchal data attributes.

FIG. 5 is a diagram that illustrates an example of a process 500 for processing user input to an electronic form in relation to a set of hierarchical data attributes. The process 500 is generally used to standardize different types of user inputs provided on the customized electronic forms in order to enable the system to track patterns associated with user activity, user behavior, and/or user patterns. For instance, different electronic forms can be configured to collect different types of information. As an example, one form can be used to evaluate user activity level by collecting exercise data submitted by the user, whereas another form can be used to track caloric intake by collecting dietary information submitted by the user. The process 500 can be used to standardize the data collected by different electronic forms, or different parts of a single electronic form so that the system can then make diagnostic inferences and/or determinations based on the collected data across multiple forms.

In general, collected data is standardized categorizing different data types within hierarchies of information, and then obtaining attributes that can be then be analyzed by the system in relation to attributes of another type of input. For example, a user's exercise journal can include text segments corresponding to different exercises performed by the user. The system can then identify the average number of calories burned by performing each exercise in order to standardize the textual input in a number of calories burned by the user as a result of performing the exercises. In another example, a user's dietary journal with foods consumed can be standardized by identifying the number of calories consumed by the user. The system can finally then relate the different types of user input provided on the exercise journal and on the dietary journal by relating the calories consumed and the calories burned.

In the example depicted in FIG. 5, the electronic form 510 is initially presented to a user to request information relating to his diet. The user provides a text query of "1 APPLE" into a text field to indicate that he has eaten an apple. The application 232 then processes the received text in relation to a hierarchy of categories 520. For instance, the application 232 may use natural language processing techniques to identify the query "APPLE" as corresponding to an element 522 within the hierarchy 520.

Each element within the hierarchy 520 includes a set of attributes that are generated based on the categories represented within the hierarchy. In the example, the hierarchy categorizes different of food groups, such as meats and fruit, and further categorizes each food groups into different constituent that fit within the same category (e.g., different types of fruit). Each element within the hierarchy 520 is associated with a set of nutritional attributes that relate to, for example, the estimated number of calories, total fat, sedum, total carbohydrates, and protein are included in one serving of each element.

In response to determining that the text submitted by the user corresponds to the element 522, the application 232 then obtains the information included within the set of attributes 530. The application then generates a table 542 that includes information related to the user input (e.g., user and date), the input provided by the user, and the set of attributes associated with the corresponding element within the hierarchy 520. The table 542 is then stored in user data 540, which stores user input data for analyzing user input on the electronic form 510.

The conversion to a common data format, or the assignment of a category or data type to an input, can be done by the user device and/or by the server. In some implementations, there are multiple databases available for administrators to select data types and category hierarchies from, e.g., a food database, a medication database, a fact database, and so on.

In some implementations, individual data types can be defined, and each data type can have a number of data type properties defined. The data type properties may represent an amount or other value obtained through user input, sensor data, or other sources. The data type properties can be assigned values based on the acquired information, e.g., to represent a number food servings, a number of caplets for medication, a body weight, and so on. A data type can have other properties defined, for example, pre-programmed information about a typical calorie content, sugar content, etc., of a food can be stored in association with that food's data type, to provide information for all instances of the data type. A data type may have a conversion parameter, a unit specification (e.g., milligrams, meters, calories, etc.), and/or other information associated with it. Other information may be associated with a data type, such as an identifier for obtaining external information, e.g., a record in another database, a URL for an image file representing the item corresponding to the data type, and so on. Groups of one or more data types can be organized into data type categories (e.g., fruit, pain medication, body vitals, etc.), and groups of one or more data type categories can be organized into data type root categories (e.g., food, medication, measurement, etc.). These hierarchies can provide consistency across the data gathered from different versions of electronic forms and across electronic forms used by different organizations.

Each entry can be associated with one or more higher-level data type categories, such as food, medication, body vital information, and so on.

The processing technique depicted in FIG. 5 illustrates how the application 232 can obtain information related to a user input provided on an electronic form, identify how the related information is categorized within a corresponding hierarchy, and store the information using relationships of categories. In this regard, user inputs of different data formats can be converted to a common data format based on using different hierarchies coincide with specific data formats. For example, input relating to a user's diet, as illustrated in FIG. 4, can be converted based on nutritional attributes of food included in the user's diet, whereas input relating to a user's activity level can be converted based on the calorie loss associated with exercises performed by the user. The converted information can then be compared and/or evaluated in order to make diagnostic inferences and/or determinations relating to the user's progress in relation a particular health condition.

As another example, an administrator that creates an electronic form can define a data type of "weight." Weight data type can be collected from many different electronic forms, in a variety of formats. In one form, a user may be prompted to manually enter a weight value via a keypad. In another form, a user may be prompted to manually select their weight from a scrollable wheel. In both cases, the form definition will specify that the collected value should be stored as a "weight" data type. The client device and/or the server system it communicate with can also convert varied inputs (e.g., text, button selection, keypad entries, etc.) to a consistent standard format. In this manner, the user-facing experiences can be customized for the audience, while retaining a clean, concise data structure. In addition, by abstracting the user-facing layer of the experience from the underlying data structure, the system can provide an essentially unlimited personalization capability while retaining the ability to perform disciplined data science at the server.

FIG. 6 is a diagram that illustrates an example of a performance analysis report 610 for an electronic form. The report 610 provides the administrator with information relating to how a user or a collection of users performed on a particular electronic form (e.g., referred to as "Form A"). In the examples depicted, the report 610 includes a region 612 representing overall completion rate, a region 614 representing an average time spent completing the form, and a region 616 representing suggested form updates across all users that completed the form.

The report 610 includes additional performance information for users of two age demographics (e.g., younger than 50 years, and older than 50 years old) and compares the performance with respect to the performance categories provided. As illustrated, users that were older than 50 years had greater difficulty completing Form A compared to users that were younger than 50 years (e.g., 62% compared to 96%). In addition, users that were older than 50 years old spent 8 more minutes on Form A on average compared to users that were younger than 50 years old (e.g., 11 minutes compared to 3 minutes).

As described above with respect to FIG. 2, the performance data relating to the electronic forms can be used to provide automated recommendations within a performance report. In the example, because users that were older than 50 years had a lower rate of completion and a higher time spent on Form A, the system determines that the current configuration of the form may be too complex for users within this age demographic. Thus, the report 610 includes a recommendation to reduce the form complexity in order to improve performance of users within this age demographic on the form. In comparison, due to high completion rate and low amount of time spent on the form by users that were younger than 50 years, the report 610 includes a recommendation to maintain the current form for users within this demographic.

Performance reports such as the report 610 can be generated by the application server 220 or the administrator system 210 in order to provide administrators with feedback on customized electronic forms that are designed on the configuration interface 212 and displayed to users through the application 232. In this regard, information included within the performance reports can be adjust the form definitions of the customized electronic forms in order to improve user engagement on the application 232. As described above, in some instances, the performance information can be used to allow manual adjustment by the administrators through the configuration interface 212, whereas in other instances, the performance information can be used in automated algorithms to dynamically update the form definitions without any intervention by the administrators. In the second instance, periodic automatic adjustments to a customized electronic form can be used to fine-tune or tailor the electronic form specifically towards the needs of an individual user or a collection of users based on prior user input data received on prior instances of the electronic form.

In general, the performance reports can indicate measures (e.g., scores, charts, graphics, etc.) that indicate the feasibility, validity, usefulness, and usability of forms that an administrator has designed.

Figure 7A:
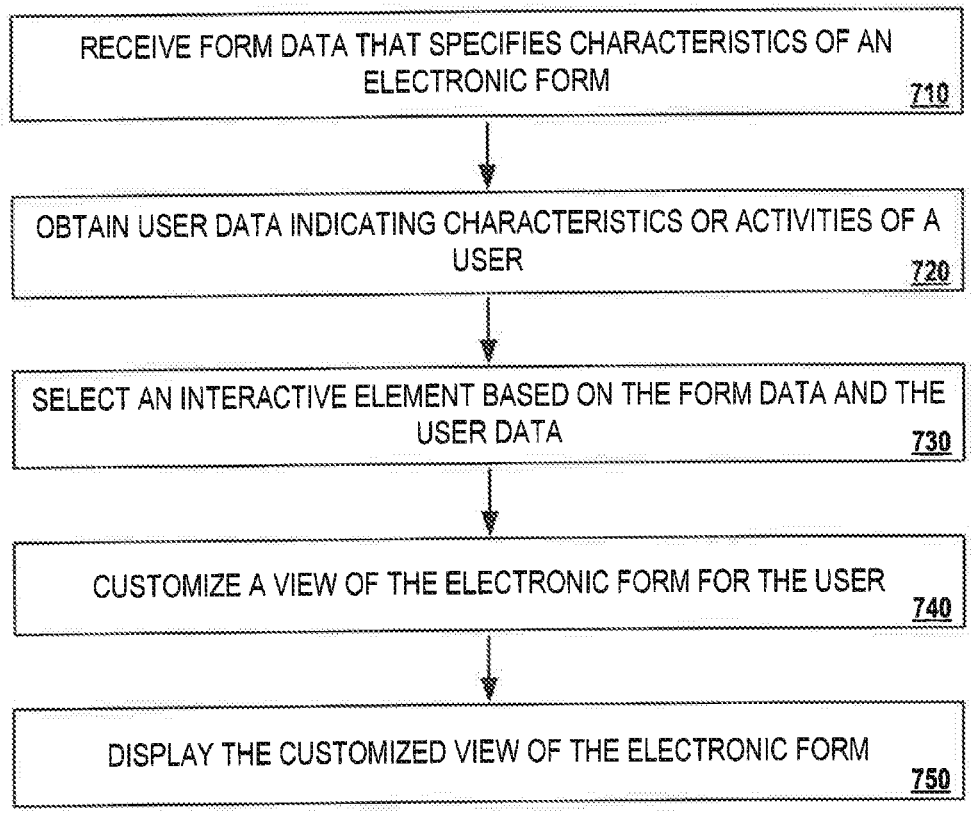
FIG. 7A is a diagram that illustrates an example of a process for displaying a customized electronic form to a user.

FIG. 7A is a diagram that illustrates an example of a process 700A for displaying a customized electronic form to a user. Briefly, the process 700A may include receiving form data that specifies characteristics of an electronic form (710), obtaining data indicating characteristics or activities of a user (720), selecting an interactive element based on the form data and the user data (730), customizing a view of the electronic form for the user (740), and displaying the customized view of the electronic form (750).

In more detail, the process 700A may include receiving form data that specifies characteristics of an electronic form (710). For instance, the user device 230 may receive form data that specifies characteristics of an electronic form over the network 205. As described above, the form data can include rules configured to vary the content of the electronic form that is presented for different users. The characteristics of the form can include a desired level of precision for information presented on the electronic form, the way in which input data is received by the electronic form, actions to be performed in response to a satisfaction of triggers and/or conditions specified for the rules, the sequence of sections within the electronic form, and/or the content that is provided on the electronic form. In some instances, the form data may also define validation rules that specify requirements for user input on the electronic form.

In some implementations, the form data is configured to cause the user device 230 to obtain user input to the electronic form, and additional data from additional sources (e.g., passively-sensed sensor data, actively-sensed sensor data, data from a sensor of the user device 230, data from a device wirelessly connected to the user device 230, or data from a third-party API). As described above the form data can be used to direct the user device 230 to obtain such data in response to certain conditions and/or triggers specified by rules included within the form data.

The form data includes various types of rules as described above. In one example, a rule can specify one or more triggers to initiate system actions specified by the rule, one or more conditions to evaluate for the rule, and one or more actions to be performed based on the condition. In some instances, the rules can include a validation rule that specifies requirements for user input to a portion of the electronic form. As described above, the validation rules can be used to determine that a user input does not satisfy a set of requirements indicated by the validation rule, and in response, the application 232 may restrict submission of data through the electronic form based on determining that the user input does not satisfy the validation rule. As an example, if an electronic form requests a user to complete an assessment, and the user provides incorrect and/or insufficient responses, the application 232 may automatically restrict further input from the user based on determining, based on the failure of the user input to satisfy a validation rule, that the user is probably confused by the way in which the electronic form is displayed on the application 232.

In some implementations, the form data specifies a data type for user input collected through the electronic form. The form data can then be used to select an interactive element to receive user input of the specified data type. In such implementations, the interactive element can be selected from among different interactive elements that each receive input of the specified data type. The selected interactive element can then be included within a customized view of the electronic form. As an example, the form data can indicate the collection of numerical data for a weight assessment form. The application 232 can then select from among different types of data entry fields that each collect numerical input from the user but with different levels of precision as illustrated in FIG. 1. In this example, the application 232 may select a data entry field that represents the appropriate level of precision based on variety of factors such as, for example, demographic information of the user or previous inputs from the user indicating a level of comprehension relating to the electronic form.

In some implementations, the electronic form includes multiple sections displayed in a sequence. The content provided in the sections can be customized based on the rules that included within the form definition for the electronic form. For example, the rules may specify the display of types of content on a particular section in response to receiving user input on the application 232 in relation to the particular section.

The process 700A may include obtaining data indicating characteristics or activities of a user (720). For instance, the user device 230 may receive user data indicating characteristics or activities of the user. As described above, user characteristics can include demographic information associated with the user, a medical history/condition associated with the user, and/or user preferences for engagement through the application 232. Examples of user activities can include input data received from devices wirelessly connected to the user device 230 (e.g., pedometer data, sleep pattern data), user inputs provided on the application 232 (e.g., prior text queries, submitted search queries, prior user selections), data received from third party APIs (e.g., list of background apps used by the user while completed the electronic form, data associated with a social media profile), or data obtained from sensors of the user device 230 (e.g., accelerometer data, location data, microphone data).

The process 700A may include selecting an interactive element based on the form data and the user data (730). For instance, the application 232 may select an interactive element from among a set of multiple interactive elements based on the user data and the rules in the received from data. For example, this may refer to selecting a particular interaction element from a set of alternative interaction elements based on the user's preferences for engagement on the application 232 (e.g., selecting a slider interface over a text input box based on a user data indicating greater frequency of usage of the former over the later. In another example, this may refer to selecting an optimal precision level for information to be provided on the electronic form based on requirements set forth by the administrator (e.g., maximal user burden, requested completion rate, speed of completion). In this example, the application 232 may dynamically identify an optimal level of precision based on the information indicated by the user data, and select from among alternative form configurations of different precision levels.

The process 700A may include customizing a view of the electronic form for the user (740). For instance, the user device 230 may customize a view of the electronic form for the user by including, in the customized view, the interactive element selected based on the user data and the rules in the received form data. For example, the selected interactive element may be used to dynamically construct or adjust the display the electronic form on the application 232. As described above, in some instances, this process may be performed in real-time such that the customization of the electronic form may be performed while the user is presently using the application 232 without requiring an additional application-wide update from the application server 220.

The process 700A may include displaying the customized view of the electronic form (750). For instance, the user device 230 may display the view of the customized electronic form on the application 232.

Figure 7B:
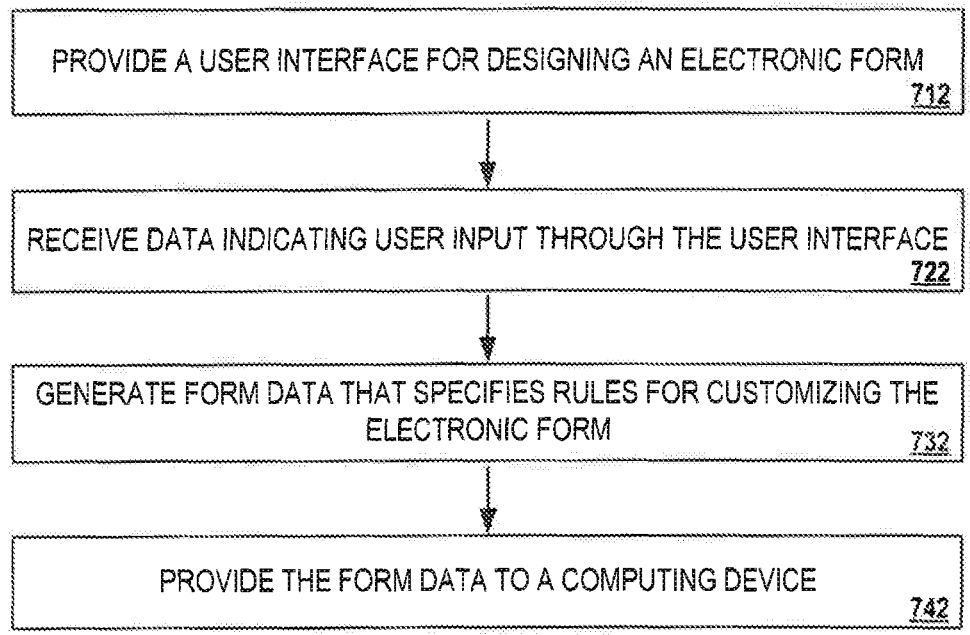
FIG. 7B is a diagram that illustrates an example of a process for generating a form definition for customizing an electronic form.

FIG. 7B is a diagram that illustrates an example of a process 700B for generating a form definition for customizing an electronic form. Briefly, the process 700B may include providing an interface for designing an electronic form (712), receiving data indicating user input through the user interface (722), generating form data that specifies rules for customizing the electronic form (732), and providing the form data to an electronic computing device (742).

In more detail, the process 700B may include providing an interface for designing an electronic form (712). For instance, the administrator system 210 may provide a configuration interface 212 for designing an electronic form for collecting data about the user of the user device 230. As described previously with respect to FIGS. 3 and 4, the configuration interface 212 enables the administrator to customize a form definition that configures or adjusts the display of the electronic form on the application 232.

The process 700B may include receiving data indicating user input through the user interface (722). For instance, the administrator system 210 may receive data indicating user input by the administrator through the configuration interface. The user input may indicate data types for data to collect using the electronic form and layout parameters for the electronic form. As described above, the administrator may specify data types for user input (e.g., numerical input, textual input, voice input) based on the purpose of the electronic form. The administrator may also specify layout parameters that adjust the presentation of the electronic form and/or the interactivity of the electronic form with the user through the application 232. For example, the administrator may select interactive elements to include within the electronic form, adjust the adjustment of the selected interactive elements in a particular layout, and/or configure other graphical attributes associated with the electronic form.

The process 700B may include generating form data that specifies rules for customizing the electronic form (732). For instance, the administrator system 210 may generate form data that specifies rules for customizing the electronic form. As described above, the form data includes a form definition that includes, among other types of specifications, rules that adjust the configuration of the electronic form based on the satisfaction of associated triggers and/or conditions that are specified by the administrator. As an example, a rule can be used to change the content provided on the electronic form based on the satisfaction of triggers and/or conditions that are each associated with different types of users. In this regard, the rules specified by the form definition can be used to vary content provided on the same electronic form that are provided to different users.

The process 700B may include providing the form data to an electronic computing device (742). For instance, the administrator system 210 or the application server 220 may transmit the form data to the user device 230 to configure or adjust the display of the electronic form on the application 232. As described above with respect to FIG. 2, the form data that is provided can be used to initially configure a new electronic form to be displayed within the application 232, or adjust the configuration of an existing electronic form that has been previously displayed to the user. In the second instance, the transmitted form data can be processed by the user device in real-time in order to dynamically adjust the existing electronic form in real-time without any intervention by the user. This technique can be used to automatically adjust the electronic form in response to user input data received on the application 232, or manually adjust the electronic forms in response to updates to the form definition provide by the administrator on the configuration interface 212.

Figure 8:
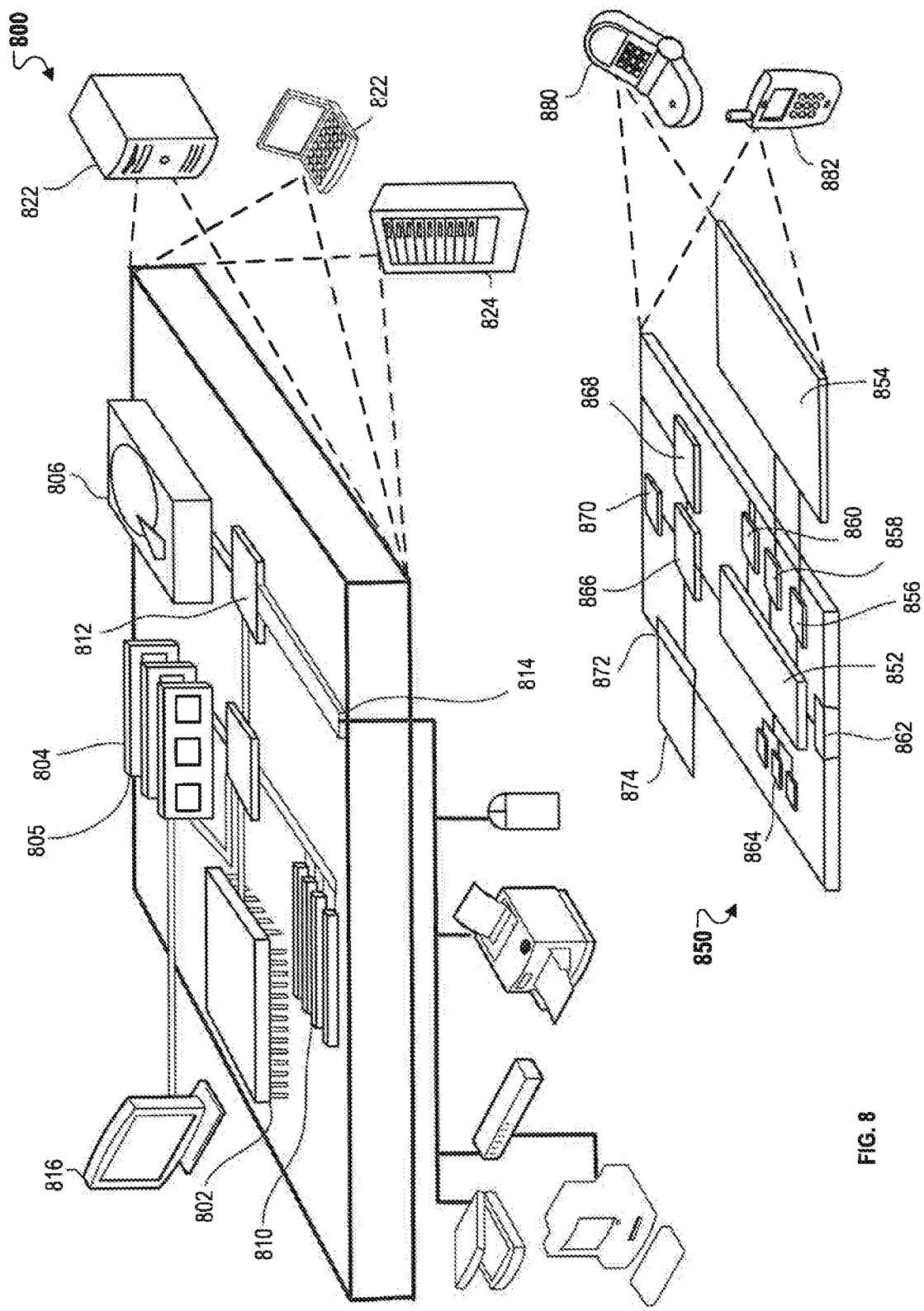
FIG. 8 is a block diagram of computing devices on which the processes described herein, or portion thereof, may be implemented.

FIG. 8 is a block diagram of computing devices 800, 850 that can be used to implement the systems and methods described in this document, as either a client or as a server or plurality of servers. Computing device 800 is intended to represent various forms of digital computers, such as laptops, desktops, workstations, personal digital assistants, servers, blade servers, mainframes, and other appropriate computers. Computing device 850 is intended to represent various forms of mobile devices, such as personal digital assistants, cellular telephones, smartphones, and other similar computing devices. Additionally, computing device 800 or 850 can include Universal Serial Bus (USB) flash drives. The USB flash drives can store operating systems and other applications. The USB flash drives can include input/output components, such as a wireless transmitter or USB connector that can be inserted into a USB port of another computing device. The components shown here, their connections and relationships, and their functions, are meant to be exemplary only, and are not meant to limit implementations of the inventions described and/or claimed in this document.

Computing device 800 includes a processor 802, memory 804, a storage device 806, a high-speed interface 808 connecting to memory 804 and high-speed expansion ports 810, and a low speed interface 812 connecting to low speed bus 814 and storage device 806. Each of the components 802, 804, 806, 808, 810, and 812, are interconnected using various busses, and can be mounted on a common motherboard or in other manners as appropriate. The processor 802 can process instructions for execution within the computing device 800, including instructions stored in the memory 804 or on the storage device 806 to display graphical information for a GUI on an external input/output device, such as display 816 coupled to high speed interface 808. In other implementations, multiple processors and/or multiple buses can be used, as appropriate, along with multiple memories and types of memory. Also, multiple computing devices 800 can be connected, with each device providing portions of the necessary operations, e.g., as a server bank, a group of blade servers, or a multi-processor system.

The memory 804 stores information within the computing device 800. In one implementation, the memory 804 is a volatile memory unit or units. In another implementation, the memory 804 is a non-volatile memory unit or units. The memory 804 can also be another form of computer-readable medium, such as a magnetic or optical disk.

The storage device 806 is capable of providing mass storage for the computing device 800. In one implementation, the storage device 806 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The information carrier is a computer- or machine-readable medium, such as the memory 804, the storage device 806, or memory on processor 802.

The high speed controller 808 manages bandwidth-intensive operations for the computing device 800, while the low speed controller 812 manages lower bandwidth intensive operations. Such allocation of functions is exemplary only. In one implementation, the high-speed controller 808 is coupled to memory 804, display 816, e.g., through a graphics processor or accelerator, and to high-speed expansion ports 810, which can accept various expansion cards (not shown). In the implementation, low-speed controller 812 is coupled to storage device 806 and low-speed expansion port

814. The low-speed expansion port, which can include various communication ports, e.g., USB, Bluetooth, Ethernet, wireless Ethernet can be coupled to one or more input/output devices, such as a keyboard, a pointing device, microphone/speaker pair, a scanner, or a networking device such as a switch or router, e.g., through a network adapter. The computing device 800 can be implemented in a number of different forms, as shown in the figure. For example, it can be implemented as a standard server 820, or multiple times in a group of such servers. It can also be implemented as part of a rack server system 824. In addition, it can be implemented in a personal computer such as a laptop computer 822. Alternatively, components from computing device 800 can be combined with other components in a mobile device (not shown), such as device 850. Each of such devices can contain one or more of computing device 800, 850, and an entire system can be made up of multiple computing devices 800, 850 communicating with each other.

The computing device 800 can be implemented in a number of different forms, as shown in the figure. For example, it can be implemented as a standard server 820, or multiple times in a group of such servers. It can also be implemented as part of a rack server system 824. In addition, it can be implemented in a personal computer such as a laptop computer 822. Alternatively, components from computing device 800 can be combined with other components in a mobile device (not shown), such as device 850. Each of such devices can contain one or more of computing device 800, 850, and an entire system can be made up of multiple computing devices 800, 850 communicating with each other.

Computing device 850 includes a processor 852, memory 884, and an input/output device such as a display 854, a communication interface 866, and a transceiver 888, among other components. The device 850 can also be provided with a storage device, such as a microdrive or other device, to provide additional storage. Each of the components 850, 852, 884, 854, 866, and 888, are interconnected using various buses, and several of the components can be mounted on a common motherboard or in other manners as appropriate.

The processor 852 can execute instructions within the computing device 850, including instructions stored in the memory 884. The processor can be implemented as a chipset of chips that include separate and multiple analog and digital processors. Additionally, the processor can be implemented using any of a number of architectures. For example, the processor 810 can be a CISC (Complex Instruction Set Computers) processor, a RISC (Reduced Instruction Set Computer) processor, or a MISC (Minimal Instruction Set Computer) processor. The processor can provide, for example, for coordination of the other components of the device 850, such as control of user interfaces, applications run by device 850, and wireless communication by device 850.

Processor 852 can communicate with a user through control interface 858 and display interface 856 coupled to a display 854. The display 854 can be, for example, a TFT (Thin-Film-Transistor Liquid Crystal Display) display or an OLED (Organic Light Emitting Diode) display, or other appropriate display technology. The display interface 856 can include appropriate circuitry for driving the display 854 to present graphical and other information to a user. The control interface 858 can receive commands from a user and convert them for submission to the processor 852. In addition, an external interface 882 can be provide in communication with processor 852, so as to enable near area communication of device 850 with other devices. External interface 882 can provide, for example, for wired communication in some implementations, or for wireless communication in other implementations, and multiple interfaces can also be used.

The memory 884 stores information within the computing device 850. The memory 884 can be implemented as one or more of a computer-readable medium or media, a volatile memory unit or units, or a non-volatile memory unit or units. Expansion memory 884 can also be provided and connected to device 850 through expansion interface 882, which can include, for example, a SIMM (Single In Line Memory Module) card interface. Such expansion memory 884 can provide extra storage space for device 850, or can also store applications or other information for device 850. Specifically, expansion memory 884 can include instructions to carry out or supplement the processes described above, and can include secure information also. Thus, for example, expansion memory 884 can be provide as a security module for device 850, and can be programmed with instructions that permit secure use of device 850. In addition, secure applications can be provided via the SIMM cards, along with additional information, such as placing identifying information on the SIMM card in a non-hackable manner.

The memory can include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 884, expansion memory 884, or memory on processor 852 that can be received, for example, over transceiver 888 or external interface 882.

Device 850 can communicate wirelessly through communication interface 866, which can include digital signal processing circuitry where necessary. Communication interface 866 can provide for communications under various modes or protocols, such as GSM voice calls, SMS, EMS, or MMS messaging, CDMA, TDMA, PDC, WCDMA, CDMA2000, or GPRS, among others. Such communication can occur, for example, through radio-frequency transceiver 888. In addition, short-range communication can occur, such as using a Bluetooth, Wi-Fi, or other such transceiver (not shown). In addition, GPS (Global Positioning System) receiver module 880 can provide additional navigation- and location-related wireless data to device 850, which can be used as appropriate by applications running on device 850.

Device 850 can also communicate audibly using audio codec 880, which can receive spoken information from a user and convert it to usable digital information. Audio codec 880 can likewise generate audible sound for a user, such as through a speaker, e.g., in a handset of device 850. Such sound can include sound from voice telephone calls, can include recorded sound, e.g., voice messages, music files, etc. and can also include sound generated by applications operating on device 850.

The computing device 850 can be implemented in a number of different forms, as shown in the figure. For example, it can be implemented as a cellular telephone 480. It can also be implemented as part of a smartphone 882, personal digital assistant, or other similar mobile device.

Various implementations of the systems and methods described here can be realized in digital electronic circuitry, integrated circuitry, specially designed ASICs (application specific integrated circuits), computer hardware, firmware, software, and/or combinations of such implementations.

These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor for displaying information to the user and a keyboard and a pointing device, e.g., a mouse or a trackball by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the systems and techniques described here, or any combination of such back end, middleware, or front end components. The components of the system can be interconnected by any form or medium of digital data communication, e.g., a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications can be made without departing from the spirit and scope of the invention. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

What is claimed is:

1. A method performed by one or more computers, the method comprising
providing, by the one or more computers, user interface data for a user interface for designing an electronic form for collecting data about a user;
receiving, by the one or more computers, data indicating user input through the user interface, the user input indicating one or more data types for data to collect using the electronic form and one or more layout parameters for the electronic form;
generating, by the one or more computers, form data that specifies one or more rules for customizing the electronic form based on one or more user characteristics of the user to which the electronic form is presented; and
providing, by the one or more computers, the form data to one or more computing devices, the form data being configured to cause different versions of the electronic form to be presented to different users, according to the one or more rules, based on the different users having different characteristics.

2. The method of claim 1, further comprising:
receiving, from devices of multiple users, data collected by the electronic form associated with the form data, the received data comprising information of a particular data type that was collected in different data formats from different users;
converting the received information of the particular data type to a common data format; and
storing the converted information.

3. The method of claim 2, wherein converting the received information comprises:
accessing data indicating a hierarchy of categories;
identifying different categories in the hierarchy that correspond to the different data formats; and
converting the information of the particular data type using relationships of the categories in the hierarchy that correspond to the different data formats.

4. The method of claim 1, wherein providing the form data to the one or more computing devices comprises:
providing the form data to a computing device such that the form data updates a form definition in an application installed at the computing device without any action by a user of the computing device.

5. The method of claim 1, wherein the form data includes one or more state rules for the electronic form, where the one or more state rules cause the computing device to select, from among multiple assessment algorithms, a particular assessment algorithm according to data collected using the electronic form.

6. The method of claim 1, wherein providing the user interface data comprises providing user interface data for a user interface that indicates a set of pre-defined database fields;
wherein receiving the data indicating the user input comprises receiving data indicating selection of a particular database field; and
wherein generating the form data comprises including, in the form data, an element of the form that is personalized for a viewer of the electronic form using data for the viewer from the particular database field.

7. The method of claim 1, wherein providing the user interface data comprises providing user interface data for a user interface that enables (i) updating of the form data to change characteristics of the electronic form and (ii) publication of the updated form data to cause an application installed on remote computing devices to update the characteristics of the electronic form in real time.

8. The method of claim 1, wherein the electronic form comprises multiple sections shown in different views;
wherein receiving data indicating the user input comprises receiving data indicating rules configured to cause different transitions among the sections of the electronic form based on data collected by the electronic form.

9. The method of claim 1, wherein generating the form data comprises generating the form data to direct a computing device presenting the electronic form to capture data from one or more additional data sources that comprise at least a device wirelessly connected to the computing device, a third-party API, or a sensor of the computing device.

10. The method of claim 1, wherein providing the user interface data comprises providing user interface data for a user interface that permits a user to specify one or more validation requirements for data entered into the electronic form.

11. The method of claim 1, wherein the form data is configured to customize the electronic form based on data indicating the one or more user characteristics that is obtained outside the electronic form.

12. The method of claim 1, wherein the form data is configured to customize the electronic form based on data indicating the one or more user characteristics that is stored before presentation of the electronic form.

13. The method of claim 1, wherein the form data is configured to customize the electronic form based on data indicating the one or more user characteristics from a user profile of the user to which the electronic form is presented.

14. The method of claim 1, wherein the one or more user characteristics comprise at least one of an age of the user, a gender of the user, a language of the user, a dialect of the user, demographic information for the user, medical history information for the user, medical condition information for the user, a user preference of the user, a reading level of the user, a health literacy of the user, an impairment of the user, or a technology fluency of the user.

15. The method of claim 1, wherein the form data specifies a set of interactive elements for presentation in the electronic form; and
wherein the form data is configured to cause an evaluation, while the electronic form is presented, about whether certain information is available, and (ii) cause the electronic form to omit one or more of the interactive elements in the set of interactive elements based on the evaluation.

16. The method of claim 1, wherein the one or more rules comprise at least one rule specifying a condition or expression to be evaluated while the electronic form is being displayed, the at least one rule specifying an action to customize the electronic form based on a result of evaluating the condition or expression.

17. A system comprising:
one or more computers; and
one or more storage devices storing instructions that, when executed by the one or more computers, cause the one or more computers to perform operations comprising:
providing, by the one or more computers, a user interface for designing an electronic form for collecting data about a user;
receiving, by the one or more computers, data indicating user input through the user interface, the user input indicating one or more data types for data to collect using the electronic form and one or more layout parameters for the electronic form;
generating, by the one or more computers, form data that specifies one or more rules for customizing the electronic form based on one or more user characteristics of the user to which the electronic form is presented; and
providing, by the one or more computers, the form data to one or more computing devices, the form data being configured to cause different versions of the electronic form to be presented to different users, according to the one or more rules, based on the different users having different characteristics.

18. The system of claim 17, wherein the operations further comprise:
receiving, from devices of multiple users, data collected by the electronic form associated with the form data, the received data comprising information of a particular data type that was collected in different data formats from different users;
converting the received information of the particular data type to a common data format; and
storing the converted information.

19. The system of claim 17, wherein providing the form data to the one or more computing devices comprises:
providing the form data to a computing device such that the form data updates a form definition in an application installed at the computing device without any action by the user of the computing device.

20. The system of claim 17, wherein providing the user interface comprises providing a user interface that indicates a set of pre-defined database fields;
wherein receiving the data indicating the user input comprises receiving data indicating selection of a particular database field; and
wherein generating the form data comprises including, in the form data, an element of the form that is personalized for a viewer of the electronic form using data for the viewer from the particular database field.

21. The system of claim 17, wherein the electronic form comprises multiple interactive elements;
wherein receiving data indicating the user input comprises receiving data indicating rules configured to cause presentation of different subsets of the interactive elements based on data collected by the electronic form.

22. The system of claim 17, wherein generating the form data comprises generating the form data to direct a computing device presenting the electronic form to capture data from one or more additional data sources that comprise at least a device wirelessly connected to the computing device, a third-party API, or a sensor of the computing device.

23. One or more non-transitory computer-readable storage media storing computer program instructions that, when executed by one or more computers, cause the one or more computers to perform operations comprising:
providing, by the one or more computers, a user interface for designing an electronic form for collecting data about a user;
receiving, by the one or more computers, data indicating user input through the user interface, the user input indicating one or more data types for data to collect using the electronic form and one or more layout parameters for the electronic form;
generating, by the one or more computers, form data that specifies one or more rules for customizing the electronic form based on one or more user characteristics of the user to which the electronic form is presented; and
providing, by the one or more computers, the form data to one or more computing devices, the form data being configured to cause different versions of the electronic form to be presented to different users, according to the one or more rules, based on the different users having different characteristics.

24. A method performed by one or more computers, the method comprising providing, by the one or more computers, a user interface for designing an electronic form for collecting data about a user;

receiving, by the one or more computers, data indicating user input through the user interface, the user input indicating one or more data types for data to collect using the electronic form and one or more layout parameters for the electronic form;

generating, by the one or more computers, form data that specifies one or more rules for customizing the electronic form;

providing, by the one or more computers, the form data to devices that respectively correspond to different users, the form data being configured to cause different versions of the electronic form to be presented to different users receiving, from the devices that respectively correspond to the different users, data collected by the electronic form associated with the form data, the received data comprising information of a particular data type that was collected in different data formats from at least some of the different users;

converting the received information of the particular data type to a common data format; and storing the converted information.

25. A method performed by one or more computers, the method comprising providing, by the one or more computers, a user interface for designing an electronic form for collecting data about a user, wherein the user interface indicates a set of database fields;

receiving, by the one or more computers, data indicating user input through the user interface, the user input indicating one or more data types for data to collect using the electronic form and one or more layout parameters for the electronic form, wherein the data indicating the user input indicates selection of a particular database field;

generating, by the one or more computers, form data that specifies one or more rules for customizing the electronic form, the form data specifying an element of the form that is personalized for a viewer of the electronic form using data for the viewer from the particular database field; and providing, by the one or more computers, the form data to one or more computing devices, the form data being configured to cause different versions of the electronic form to be presented to different users.

\* \* \* \* \*

UNITED STATES PATENT AND TRADEMARK OFFICE
CERTIFICATE OF CORRECTION

PATENT NO. : 10,621,280 B2
APPLICATION NO. : 15/935276
DATED : April 14, 2020
INVENTOR(S) : Neeta Jain et al.

It is certified that error appears in the above-identified patent and that said Letters Patent is hereby corrected as shown below:

In the Specification

At Column 1, Line 10, please insert the following section:
-- GOVERNMENT LICENSE RIGHTS
This invention was made with government support under grant number HHSN261201500013C awarded by the National Institutes of Health. The government has certain rights in the invention. --.

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*